US011950778B2

(12) United States Patent
Balbierz et al.

(10) Patent No.: US 11,950,778 B2
(45) Date of Patent: Apr. 9, 2024

(54) TISSUE-ACQUISITION AND FASTENING DEVICES AND METHODS

(71) Applicant: Boston Scientific Scimed, Inc., Maple Grove, MN (US)

(72) Inventors: Daniel Balbierz, Redwood City, CA (US); David Cole, San Mateo, CA (US); Bretton Swope, Gaithersburg, MD (US); Pablo R. Hambly, San Mateo, CA (US); Justen England, Plymouth, MA (US); Samuel T. Crews, Palomar Park, CA (US); Craig Arthur Purdy, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 655 days.

(21) Appl. No.: 16/990,234

(22) Filed: Aug. 11, 2020

(65) Prior Publication Data
US 2021/0007739 A1  Jan. 14, 2021

Related U.S. Application Data

(63) Continuation of application No. 15/165,425, filed on May 26, 2016, now abandoned, which is a
(Continued)

(51) Int. Cl.
*A61B 17/072*    (2006.01)
*A61B 17/064*    (2006.01)
(Continued)

(52) U.S. Cl.
CPC .... *A61B 17/07207* (2013.01); *A61B 17/0643* (2013.01); *A61B 17/0644* (2013.01);
(Continued)

(58) Field of Classification Search
CPC .......... A61B 17/07207; A61B 17/0643; A61B 17/0644; A61B 17/0682
See application file for complete search history.

(56) References Cited

U.S. PATENT DOCUMENTS

| 1,408,865 A | 3/1922 | Codwell |
| 3,663,965 A | 5/1972 | Lee et al. |

(Continued)

FOREIGN PATENT DOCUMENTS

| AU | 629664 | 2/1991 |
| CH | 680263 A5 | 7/1992 |

(Continued)

OTHER PUBLICATIONS

International Search Report from PCT Patent Application No. PCT/US2002/027177 dated Feb. 14, 2003.
(Continued)

*Primary Examiner* — Nathaniel C Chukwurah
(74) *Attorney, Agent, or Firm* — Bookoff McAndrews, PLLC

(57) ABSTRACT

Devices and methods for acquiring and fastening tissues folds within an internal organ, such as the stomach, and for applying the methods and devices to producing reductions in organ volume or repair of bariatric procedures, are disclosed. An exemplary method for forming a continuous laterally extending tissue fold involves forming a succession of laterally extending folds having adjacent overlapping fold portions. One exemplary tissue-acquisition device has an open-end roller-and-arm structure that allows individual tissue folds to be formed and fastened, then advanced to an adjacent region within the stomach, for capture of a new fold that will form an extension of the existing fold(s).

18 Claims, 20 Drawing Sheets

Related U.S. Application Data continuation of application No. 13/112,664, filed on May 20, 2011, now abandoned.

(60) Provisional application No. 61/347,345, filed on May 21, 2010.

(51) Int. Cl.
    *A61B 17/068*      (2006.01)
    *A61F 5/00*      (2006.01)
    *A61B 17/00*      (2006.01)
    *A61B 17/08*      (2006.01)
    *A61B 17/29*      (2006.01)
    *A61B 17/30*      (2006.01)

(52) U.S. Cl.
    CPC ...... *A61B 17/0682* (2013.01); *A61B 17/0684* (2013.01); *A61B 17/0686* (2013.01); *A61B 17/072* (2013.01); *A61F 5/0086* (2013.01); *A61B 2017/00818* (2013.01); *A61B 2017/07214* (2013.01); *A61B 2017/081* (2013.01); *A61B 2017/2926* (2013.01); *A61B 2017/306* (2013.01)

(56) References Cited

U.S. PATENT DOCUMENTS

| | | |
|---|---|---|
| 4,134,405 A | 1/1979 | Smit |
| 4,207,890 A | 6/1980 | Mamajek et al. |
| 4,246,893 A | 1/1981 | Berson |
| 4,315,509 A | 2/1982 | Smit |
| 4,331,277 A | 5/1982 | Green |
| 4,403,604 A | 9/1983 | Wilkinson et al. |
| 4,416,267 A | 11/1983 | Garren et al. |
| 4,417,360 A | 11/1983 | Moasser |
| 4,441,215 A | 4/1984 | Kaster |
| 4,467,804 A | 8/1984 | Hardy et al. |
| 4,485,805 A | 12/1984 | Foster, Jr. |
| 4,488,523 A | 12/1984 | Shichman |
| 4,501,264 A | 2/1985 | Rockey |
| 4,607,618 A | 8/1986 | Angelchik |
| 4,612,933 A | 9/1986 | Brinkerhoff et al. |
| 4,617,932 A | 10/1986 | Kornberg |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,747,849 A | 5/1988 | Galitier |
| 4,846,836 A | 7/1989 | Reich |
| 4,848,367 A | 7/1989 | Avant et al. |
| 4,899,747 A | 2/1990 | Garren et al. |
| 4,925,446 A | 5/1990 | Garay et al. |
| 4,946,440 A | 8/1990 | Hall |
| 4,969,896 A | 11/1990 | Shors |
| 4,997,084 A | 3/1991 | Opie et al. |
| 5,006,106 A | 4/1991 | Angelchik |
| 5,037,021 A | 8/1991 | Mills et al. |
| 5,061,275 A | 10/1991 | Wallsten et al. |
| 5,084,061 A | 1/1992 | Gau et al. |
| 5,088,979 A | 2/1992 | Filipi et al. |
| 5,163,952 A | 11/1992 | Froix |
| 5,211,658 A | 5/1993 | Clouse |
| 5,234,454 A | 8/1993 | Bangs |
| 5,246,456 A | 9/1993 | Wilkinson |
| 5,259,399 A | 11/1993 | Brown |
| 5,263,629 A | 11/1993 | Trumbull et al. |
| 5,282,484 A | 2/1994 | Reger |
| 5,290,217 A | 3/1994 | Campos |
| 5,306,300 A | 4/1994 | Berry |
| 5,314,473 A | 5/1994 | Godin |
| 5,327,914 A | 7/1994 | Shlain |
| 5,345,949 A | 9/1994 | Shlain |
| 5,355,897 A | 10/1994 | Pietrafitta et al. |
| 5,401,241 A | 3/1995 | Delany |
| 5,403,326 A | 4/1995 | Harrison et al. |
| 5,405,377 A | 4/1995 | Cragg |
| 5,417,703 A | 5/1995 | Brown et al. |
| 5,431,673 A | 7/1995 | Summers et al. |
| 5,486,187 A | 1/1996 | Schneck |
| 5,514,176 A | 5/1996 | Smit |
| 5,535,935 A | 7/1996 | Vidal et al. |
| 5,542,949 A | 8/1996 | Yoon |
| 5,562,239 A | 10/1996 | Boiarski et al. |
| 5,571,116 A | 11/1996 | Bolanos et al. |
| 5,577,654 A | 11/1996 | Bishop |
| 5,593,434 A | 1/1997 | Williams |
| 5,597,107 A | 1/1997 | Knodel et al. |
| 5,609,624 A | 3/1997 | Kalis |
| 5,628,786 A | 5/1997 | Banas et al. |
| 5,630,539 A | 5/1997 | Plyley et al. |
| 5,647,526 A | 7/1997 | Green et al. |
| 5,653,743 A | 8/1997 | Martin |
| 5,662,713 A | 9/1997 | Andersen et al. |
| 5,673,841 A | 10/1997 | Schulze et al. |
| 5,674,241 A | 10/1997 | Bley et al. |
| 5,676,674 A | 10/1997 | Bolanos et al. |
| 5,706,998 A | 1/1998 | Plyley et al. |
| 5,709,657 A | 1/1998 | Zimmon |
| 5,720,776 A | 2/1998 | Chuter et al. |
| 5,749,918 A | 5/1998 | Hogendjijk et al. |
| 5,762,255 A | 6/1998 | Chrisman et al. |
| 5,771,903 A | 6/1998 | Jakobsson |
| 5,785,684 A | 7/1998 | Zimmon |
| 5,792,119 A | 8/1998 | Marx |
| 5,820,584 A | 10/1998 | Crabb |
| 5,839,639 A | 11/1998 | Sauer et al. |
| 5,848,964 A | 12/1998 | Samuels |
| 5,855,311 A | 1/1999 | Hamblin et al. |
| 5,855,601 A | 1/1999 | Bessler et al. |
| 5,856,445 A | 1/1999 | Korsmeyer |
| 5,861,036 A | 1/1999 | Godin |
| 5,865,361 A | 2/1999 | Milliman et al. |
| 5,868,141 A | 2/1999 | Ellias |
| 5,868,760 A | 2/1999 | McGuckin, Jr. |
| 5,887,594 A | 3/1999 | LoCicero, III |
| 5,897,562 A | 4/1999 | Bolanos et al. |
| 5,910,144 A | 6/1999 | Hayashi et al. |
| 5,922,019 A | 7/1999 | Hankh et al. |
| 5,947,983 A | 9/1999 | Solar et al. |
| 5,993,473 A | 11/1999 | Chan et al. |
| 5,993,483 A | 11/1999 | Gianotti |
| 6,016,848 A | 1/2000 | Egrees |
| 6,036,641 A | 3/2000 | Taylor et al. |
| 6,051,015 A | 4/2000 | Maahs |
| 6,086,600 A | 7/2000 | Kortenbach |
| 6,098,629 A | 8/2000 | Johnson et al. |
| 6,102,922 A | 8/2000 | Jakobsson et al. |
| 6,113,609 A | 9/2000 | Adams |
| 6,119,913 A | 9/2000 | Adams et al. |
| 6,120,534 A | 9/2000 | Ruiz |
| 6,126,058 A | 10/2000 | Adams et al. |
| 6,146,416 A | 11/2000 | Andersen et al. |
| 6,159,146 A | 12/2000 | El Gazayerli |
| 6,159,238 A | 12/2000 | Killion et al. |
| 6,179,195 B1 | 1/2001 | Adams et al. |
| 6,197,022 B1 | 3/2001 | Baker |
| 6,206,930 B1 | 3/2001 | Burg et al. |
| 6,245,088 B1 | 6/2001 | Lowery |
| 6,251,132 B1 | 6/2001 | Ravenscroft et al. |
| 6,254,642 B1 | 7/2001 | Taylor |
| 6,258,120 B1 | 7/2001 | McKenzie et al. |
| 6,264,700 B1 | 7/2001 | Kilcoyne et al. |
| 6,287,334 B1 | 9/2001 | Moll et al. |
| 6,302,917 B1 | 10/2001 | Dua et al. |
| 6,358,197 B1 | 3/2002 | Silverman et al. |
| 6,383,195 B1 | 5/2002 | Richard |
| 6,416,522 B1 | 7/2002 | Strecker |
| 6,425,900 B1 | 7/2002 | Knodel et al. |
| 6,425,916 B1 | 7/2002 | Garrison et al. |
| 6,454,785 B2 | 9/2002 | De Hoyos Garza |
| 6,460,543 B1 | 10/2002 | Forsell |
| 6,461,366 B1 | 10/2002 | Seguin |
| 6,494,888 B1 | 12/2002 | Laufer et al. |

(56) References Cited

U.S. PATENT DOCUMENTS

| | | |
|---|---|---|
| 6,494,895 B2 | 12/2002 | Addis |
| 6,503,264 B1 | 1/2003 | Birk |
| 6,506,196 B1 | 1/2003 | Laufer et al. |
| 6,527,784 B2 | 3/2003 | Adams et al. |
| 6,540,789 B1 | 4/2003 | Silverman et al. |
| 6,544,271 B1 | 4/2003 | Adams et al. |
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor |
| 6,572,627 B2 | 6/2003 | Gabbay |
| 6,572,629 B2 | 6/2003 | Kalloo |
| 6,575,896 B2 | 6/2003 | Silverman et al. |
| 6,592,596 B1 | 7/2003 | Geitz et al. |
| 6,596,023 B1 | 7/2003 | Nunez et al. |
| 6,607,555 B2 | 8/2003 | Patterson et al. |
| 6,627,206 B2 | 9/2003 | Lloyd |
| 6,632,227 B2 | 10/2003 | Adams |
| 6,663,639 B1 | 12/2003 | Laufer et al. |
| 6,675,809 B2 | 1/2004 | Stack et al. |
| 6,733,512 B2 | 5/2004 | McGhan |
| 6,740,098 B2 | 5/2004 | Abrams et al. |
| 6,740,121 B2 | 5/2004 | Geitz et al. |
| 6,746,460 B2 | 6/2004 | Gannoe et al. |
| 6,755,869 B2 | 6/2004 | Geitz |
| 6,764,518 B2 | 7/2004 | Godin |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,821,285 B2 | 11/2004 | Laufer et al. |
| 6,827,246 B2 | 12/2004 | Sullivan et al. |
| 6,835,200 B2 | 12/2004 | Laufer et al. |
| 6,845,776 B2 | 1/2005 | Stack et al. |
| 6,916,332 B2 | 7/2005 | Adams |
| 6,932,838 B2 | 8/2005 | Schwartz et al. |
| 6,960,233 B1 | 11/2005 | Berg et al. |
| 6,966,875 B1 | 11/2005 | Longobardi |
| 6,981,978 B2 | 1/2006 | Gannoe |
| 6,981,980 B2 | 1/2006 | Sampson et al. |
| 6,994,715 B2 | 2/2006 | Gannoe et al. |
| 7,011,094 B2 | 3/2006 | Rapackie et al. |
| 7,020,531 B1 | 3/2006 | Colliu et al. |
| 7,025,791 B2 | 4/2006 | Levine et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,056,305 B2 | 6/2006 | Garza |
| 7,059,331 B2 | 6/2006 | Adams et al. |
| 7,066,945 B2 | 6/2006 | Hashiba et al. |
| 7,083,629 B2 | 8/2006 | Weller et al. |
| 7,090,699 B2 | 8/2006 | Geitz |
| 7,097,650 B2 | 8/2006 | Weller et al. |
| 7,097,665 B2 | 8/2006 | Stack et al. |
| 7,111,627 B2 | 9/2006 | Stack et al. |
| 7,112,186 B2 | 9/2006 | Shah |
| 7,120,498 B2 | 10/2006 | Imran et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,147,140 B2 | 12/2006 | Wukusick et al. |
| 7,152,607 B2 | 12/2006 | Stack et al. |
| 7,153,314 B2 | 12/2006 | Laufer et al. |
| 7,160,312 B2 | 1/2007 | Saadat et al. |
| 7,172,613 B2 | 2/2007 | Wazne |
| 7,175,638 B2 | 2/2007 | Gannoe et al. |
| 7,175,660 B2 | 2/2007 | Cartledge et al. |
| 7,211,114 B2 | 5/2007 | Bessler et al. |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,229,453 B2 | 6/2007 | Anderson et al. |
| 7,232,445 B2 | 6/2007 | Kortenbach et al. |
| 7,255,675 B2 | 8/2007 | Gertner et al. |
| 7,261,722 B2 | 8/2007 | McGuckin, Jr. et al. |
| 7,288,101 B2 | 10/2007 | Deem et al. |
| 7,306,614 B2 | 12/2007 | Weller et al. |
| 7,315,509 B2 | 1/2008 | Jeong et al. |
| 7,316,716 B2 | 1/2008 | Egan |
| 7,320,696 B2 | 1/2008 | Gazi et al. |
| 7,326,207 B2 | 2/2008 | Edwards |
| 7,335,210 B2 | 2/2008 | Smit |
| 7,347,863 B2 | 3/2008 | Rothe et al. |
| 7,347,875 B2 | 3/2008 | Levine et al. |
| 7,354,454 B2 | 4/2008 | Stack et al. |
| 7,399,304 B2 | 7/2008 | Gambale et al. |
| 7,431,725 B2 | 10/2008 | Stack et al. |
| 7,461,767 B2 | 12/2008 | Viola et al. |
| 7,470,251 B2 | 12/2008 | Shah |
| 7,485,142 B2 | 2/2009 | Milo |
| 7,503,922 B2 | 3/2009 | Deem et al. |
| 7,520,884 B2 | 4/2009 | Swanstrom et al. |
| 7,546,939 B2 | 6/2009 | Adams et al. |
| 7,575,586 B2 | 8/2009 | Berg et al. |
| 7,608,114 B2 | 10/2009 | Levine et al. |
| 7,615,064 B2 | 11/2009 | Bjerken |
| 7,628,821 B2 | 12/2009 | Stack et al. |
| 7,662,161 B2 | 2/2010 | Briganti et al. |
| 7,670,279 B2 | 3/2010 | Gertner |
| 7,674,721 B2 | 3/2010 | Bjerken |
| 7,695,446 B2 | 4/2010 | Levine et al. |
| 7,699,863 B2 | 4/2010 | Marco et al. |
| 7,708,181 B2 | 5/2010 | Cole et al. |
| 7,713,277 B2 | 5/2010 | Laufer et al. |
| 7,717,843 B2 | 5/2010 | Balbierz et al. |
| 7,721,932 B2 | 5/2010 | Cole et al. |
| 7,731,757 B2 | 6/2010 | Taylor et al. |
| 7,744,613 B2 | 6/2010 | Ewers et al. |
| 7,744,627 B2 | 6/2010 | Orban et al. |
| 7,753,870 B2 | 7/2010 | Demarais et al. |
| 7,766,861 B2 | 8/2010 | Levine et al. |
| 7,776,057 B2 | 8/2010 | Laufer et al. |
| 7,819,836 B2 | 10/2010 | Levine et al. |
| 7,846,138 B2 | 12/2010 | Dann et al. |
| 7,846,174 B2 | 12/2010 | Baker et al. |
| 7,857,823 B2 | 12/2010 | Laufer et al. |
| 7,881,797 B2 | 2/2011 | Griffin et al. |
| 7,892,214 B2 | 2/2011 | Kagan et al. |
| 7,892,292 B2 | 2/2011 | Stack et al. |
| 7,934,631 B2 * | 5/2011 | Balbierz .............. A61B 17/072 227/176.1 |
| 8,142,450 B2 | 3/2012 | Harris et al. |
| 8,500,777 B2 | 8/2013 | Harris et al. |
| 2001/0011543 A1 | 8/2001 | Forsell |
| 2001/0020189 A1 | 9/2001 | Taylor |
| 2001/0020190 A1 | 9/2001 | Taylor |
| 2001/0021796 A1 | 9/2001 | Silverman et al. |
| 2001/0041916 A1 | 11/2001 | Bonutti |
| 2001/0044595 A1 | 11/2001 | Reydel et al. |
| 2002/0022851 A1 | 2/2002 | Kalloo et al. |
| 2002/0055750 A1 | 5/2002 | Durgin et al. |
| 2002/0055757 A1 | 5/2002 | Torre et al. |
| 2002/0072761 A1 | 6/2002 | Abrams et al. |
| 2002/0082621 A1 | 6/2002 | Shurr et al. |
| 2002/0099439 A1 | 7/2002 | Schwartz et al. |
| 2002/0128667 A1 | 9/2002 | Kobayashi et al. |
| 2002/0183767 A1 | 12/2002 | Adams et al. |
| 2002/0183768 A1 | 12/2002 | Deem et al. |
| 2002/0188354 A1 | 12/2002 | Peghini |
| 2003/0009236 A1 | 1/2003 | Godin |
| 2003/0040804 A1 | 2/2003 | Stack et al. |
| 2003/0040808 A1 | 2/2003 | Stack et al. |
| 2003/0054060 A1 | 3/2003 | Scheungraber |
| 2003/0065340 A1 | 4/2003 | Geitz |
| 2003/0065359 A1 | 4/2003 | Weller et al. |
| 2003/0093117 A1 | 5/2003 | Saadat et al. |
| 2003/0109892 A1 | 6/2003 | Deem et al. |
| 2003/0109931 A1 | 6/2003 | Geitz |
| 2003/0114773 A1 | 6/2003 | Janssens |
| 2003/0120289 A1 | 6/2003 | McGuckin, Jr. et al. |
| 2003/0158569 A1 | 8/2003 | Wazne |
| 2003/0181929 A1 | 9/2003 | Geitz |

(56) References Cited

U.S. PATENT DOCUMENTS

| | | |
|---|---|---|
| 2003/0191476 A1 | 10/2003 | Smit |
| 2003/0191525 A1 | 10/2003 | Thornton |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2003/0220660 A1 | 11/2003 | Kortenbach et al. |
| 2004/0006351 A1 | 1/2004 | Gannoe et al. |
| 2004/0010245 A1 | 1/2004 | Cerier et al. |
| 2004/0024386 A1 | 2/2004 | Deem et al. |
| 2004/0030347 A1 | 2/2004 | Gannoe et al. |
| 2004/0044353 A1 | 3/2004 | Gannoe |
| 2004/0044354 A1 | 3/2004 | Gannoe et al. |
| 2004/0044357 A1 | 3/2004 | Gannoe et al. |
| 2004/0044364 A1 | 3/2004 | DeVries et al. |
| 2004/0049251 A1 | 3/2004 | Knowlton |
| 2004/0059289 A1 | 3/2004 | Garza et al. |
| 2004/0068726 A1 | 4/2004 | Golden et al. |
| 2004/0082963 A1 | 4/2004 | Gannoe et al. |
| 2004/0088023 A1 | 5/2004 | Imran et al. |
| 2004/0092892 A1 | 5/2004 | Kagan et al. |
| 2004/0092974 A1 | 5/2004 | Gannoe et al. |
| 2004/0093091 A1 | 5/2004 | Gannoe et al. |
| 2004/0098043 A1 | 5/2004 | Trout |
| 2004/0107004 A1 | 6/2004 | Levine et al. |
| 2004/0117031 A1 | 6/2004 | Stack et al. |
| 2004/0133219 A1 | 7/2004 | Forsell |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162568 A1 | 8/2004 | Saadat et al. |
| 2004/0172141 A1 | 9/2004 | Stack et al. |
| 2004/0172142 A1 | 9/2004 | Stack et al. |
| 2004/0186502 A1 | 9/2004 | Sampson et al. |
| 2004/0193184 A1 | 9/2004 | Laufer et al. |
| 2004/0210243 A1 | 10/2004 | Gannoe et al. |
| 2004/0215216 A1 | 10/2004 | Gannoe et al. |
| 2004/0217146 A1 | 11/2004 | Beck |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0236419 A1 | 11/2004 | Milo |
| 2004/0243152 A1 | 12/2004 | Taylor et al. |
| 2004/0243223 A1 | 12/2004 | Kraemer et al. |
| 2004/0267378 A1 | 12/2004 | Gazi et al. |
| 2005/0004430 A1 | 1/2005 | Lee et al. |
| 2005/0004681 A1 | 1/2005 | Stack et al. |
| 2005/0033326 A1 | 2/2005 | Briganti et al. |
| 2005/0033345 A1 | 2/2005 | DeLegge |
| 2005/0049718 A1 | 3/2005 | Dann et al. |
| 2005/0075654 A1 | 4/2005 | Kelleher |
| 2005/0080444 A1 | 4/2005 | Kraemer et al. |
| 2005/0085787 A1 | 4/2005 | Laufer et al. |
| 2005/0096673 A1 | 5/2005 | Stack et al. |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149114 A1 | 7/2005 | Cartledge et al. |
| 2005/0159769 A1 | 7/2005 | Alverdy |
| 2005/0177176 A1* | 8/2005 | Gerbi ............ A61B 17/07207 606/139 |
| 2005/0177181 A1 | 8/2005 | Kagan et al. |
| 2005/0183732 A1 | 8/2005 | Edwards |
| 2005/0192599 A1 | 9/2005 | Demarais |
| 2005/0192615 A1 | 9/2005 | Torre et al. |
| 2005/0216040 A1 | 9/2005 | Gertner et al. |
| 2005/0216042 A1 | 9/2005 | Gertner |
| 2005/0228504 A1 | 10/2005 | Demarais et al. |
| 2005/0240279 A1 | 10/2005 | Kagan et al. |
| 2005/0245965 A1 | 11/2005 | Orban et al. |
| 2005/0247320 A1 | 11/2005 | Stack et al. |
| 2005/0250980 A1 | 11/2005 | Swanstrom et al. |
| 2005/0251158 A1 | 11/2005 | Sadat et al. |
| 2005/0251160 A1 | 11/2005 | Saadat et al. |
| 2005/0251162 A1 | 11/2005 | Rothe et al. |
| 2005/0256533 A1 | 11/2005 | Roth et al. |
| 2005/0256587 A1 | 11/2005 | Egan |
| 2005/0261712 A1 | 11/2005 | Balbierz et al. |
| 2005/0267405 A1 | 12/2005 | Shah |
| 2005/0267499 A1 | 12/2005 | Stack et al. |
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0009858 A1 | 1/2006 | Levine et al. |
| 2006/0015006 A1 | 1/2006 | Laurence et al. |
| 2006/0020278 A1 | 1/2006 | Burnette et al. |
| 2006/0025750 A1 | 2/2006 | Starksen et al. |
| 2006/0058829 A1 | 3/2006 | Sampson et al. |
| 2006/0064120 A1 | 3/2006 | Levine et al. |
| 2006/0069400 A1 | 3/2006 | Burnett et al. |
| 2006/0129094 A1 | 6/2006 | Shah |
| 2006/0151568 A1 | 7/2006 | Weller et al. |
| 2006/0155259 A1 | 7/2006 | MacLay |
| 2006/0155311 A1 | 7/2006 | Hashiba et al. |
| 2006/0155312 A1 | 7/2006 | Levine et al. |
| 2006/0161139 A1 | 7/2006 | Levine et al. |
| 2006/0161187 A1 | 7/2006 | Levine et al. |
| 2006/0178560 A1 | 8/2006 | Saadat et al. |
| 2006/0178691 A1 | 8/2006 | Binmoeller |
| 2006/0195139 A1 | 8/2006 | Gertner |
| 2006/0247662 A1 | 11/2006 | Schwartz et al. |
| 2006/0253142 A1 | 11/2006 | Bjerken |
| 2006/0271076 A1 | 11/2006 | Weller et al. |
| 2006/0282095 A1 | 12/2006 | Stokes et al. |
| 2006/0287734 A1 | 12/2006 | Stack et al. |
| 2007/0010864 A1 | 1/2007 | Dann et al. |
| 2007/0027548 A1 | 2/2007 | Levine et al. |
| 2007/0032800 A1 | 2/2007 | Oritz et al. |
| 2007/0043384 A1 | 2/2007 | Oritz et al. |
| 2007/0055292 A1 | 3/2007 | Oritz et al. |
| 2007/0060932 A1 | 3/2007 | Stack et al. |
| 2007/0149994 A1 | 6/2007 | Sosnowski et al. |
| 2007/0175488 A1 | 8/2007 | Cox et al. |
| 2007/0191870 A1 | 8/2007 | Baker et al. |
| 2007/0191871 A1 | 8/2007 | Baker et al. |
| 2007/0198074 A1 | 8/2007 | Dann et al. |
| 2007/0219571 A1 | 9/2007 | Balbierz et al. |
| 2007/0239284 A1 | 10/2007 | Skerven et al. |
| 2007/0260327 A1 | 11/2007 | Case et al. |
| 2007/0276428 A1 | 11/2007 | Haller et al. |
| 2007/0276432 A1 | 11/2007 | Stack et al. |
| 2008/0033574 A1 | 2/2008 | Bessler et al. |
| 2008/0065122 A1 | 3/2008 | Stack et al. |
| 2008/0097510 A1 | 4/2008 | Albrecht et al. |
| 2008/0116244 A1 | 5/2008 | Rethy et al. |
| 2008/0190989 A1 | 8/2008 | Crews et al. |
| 2008/0195226 A1 | 8/2008 | Williams et al. |
| 2008/0208355 A1 | 8/2008 | Stack et al. |
| 2008/0208356 A1 | 8/2008 | Stack et al. |
| 2008/0221599 A1 | 9/2008 | Starksen |
| 2008/0228030 A1 | 9/2008 | Godin |
| 2008/0234703 A1 | 9/2008 | Cropper et al. |
| 2008/0249566 A1 | 10/2008 | Harris et al. |
| 2008/0269797 A1 | 10/2008 | Stack et al. |
| 2008/0294179 A1 | 11/2008 | Balbierz et al. |
| 2008/0319455 A1 | 12/2008 | Harris et al. |
| 2008/0319471 A1 | 12/2008 | Sosnowski et al. |
| 2009/0018558 A1 | 1/2009 | Laufer et al. |
| 2009/0024143 A1 | 1/2009 | Crews et al. |
| 2009/0030284 A1 | 1/2009 | Cole et al. |
| 2009/0125040 A1 | 5/2009 | Hambley et al. |
| 2009/0171383 A1 | 7/2009 | Cole et al. |
| 2009/0177215 A1 | 7/2009 | Stack et al. |
| 2009/0182424 A1 | 7/2009 | Marco et al. |
| 2009/0236388 A1 | 9/2009 | Cole et al. |
| 2009/0236389 A1 | 9/2009 | Cole et al. |
| 2009/0236390 A1 | 9/2009 | Cole et al. |
| 2009/0236391 A1 | 9/2009 | Cole et al. |
| 2009/0236392 A1 | 9/2009 | Cole et al. |
| 2009/0236394 A1 | 9/2009 | Cole et al. |
| 2009/0236396 A1 | 9/2009 | Cole et al. |
| 2009/0236397 A1 | 9/2009 | Cole et al. |

(56) References Cited

U.S. PATENT DOCUMENTS

| | | |
|---|---|---|
| 2009/0236398 A1 | 9/2009 | Cole et al. |
| 2009/0236400 A1 | 9/2009 | Cole et al. |
| 2009/0236401 A1 | 9/2009 | Cole et al. |
| 2009/0275964 A1 | 11/2009 | Zeiner et al. |
| 2009/0287045 A1 | 11/2009 | Mitelberg et al. |
| 2009/0299487 A1 | 12/2009 | Stack et al. |
| 2010/0010293 A1 | 1/2010 | Sato et al. |
| 2010/0016988 A1 | 1/2010 | Stack et al. |
| 2010/0044410 A1 | 2/2010 | Argentine et al. |
| 2010/0100109 A1 | 4/2010 | Stack et al. |
| 2010/0116867 A1 | 5/2010 | Balbierz et al. |
| 2010/0191258 A1 | 7/2010 | Harris et al. |
| 2010/0204719 A1 | 8/2010 | Balbierz et al. |
| 2011/0098725 A1 | 4/2011 | Cox et al. |

FOREIGN PATENT DOCUMENTS

| | | |
|---|---|---|
| DE | 08708978 U1 | 11/1987 |
| EP | 0775471 | 5/1997 |
| EP | 1256318 A1 | 11/2002 |
| EP | 1492478 | 1/2005 |
| EP | 1602336 | 12/2005 |
| EP | 1754444 A2 | 2/2007 |
| FR | 2768324 | 3/1999 |
| JP | 09-168597 | 6/1997 |
| WO | WO 91/01117 | 2/1991 |
| WO | WO 95/25468 A1 | 9/1995 |
| WO | WO 97/47231 | 12/1997 |
| WO | WO 00/12027 | 3/2000 |
| WO | WO 00/32137 | 6/2000 |
| WO | WO 00/78227 | 12/2000 |
| WO | WO 01/41671 | 6/2001 |
| WO | WO 01/45485 | 6/2001 |
| WO | WO 01/49359 | 7/2001 |
| WO | WO 01/66018 | 9/2001 |
| WO | WO 01/85034 | 11/2001 |
| WO | WO 01/89393 | 11/2001 |
| WO | WO 02/060328 | 8/2002 |
| WO | WO 03/017882 | 3/2003 |
| WO | 2003077730 A2 | 9/2003 |
| WO | WO 03/086246 | 10/2003 |
| WO | WO 03/086247 | 10/2003 |
| WO | WO 03/090633 | 11/2003 |
| WO | WO 03/094784 | 11/2003 |
| WO | WO 03/094785 | 11/2003 |
| WO | WO 03/099137 | 12/2003 |
| WO | WO 03/105698 A2 | 12/2003 |
| WO | WO 04/019765 | 3/2004 |
| WO | WO 04/019787 | 3/2004 |
| WO | WO 04/032760 | 4/2004 |
| WO | WO 04/037064 | 5/2004 |
| WO | WO 04/041133 | 5/2004 |
| WO | WO 04/064680 | 8/2004 |
| WO | WO 04/064685 | 8/2004 |
| WO | WO 04/080336 | 9/2004 |
| WO | WO 04/110285 | 12/2004 |
| WO | WO 05/037152 | 4/2005 |
| WO | WO 05/079673 | 9/2005 |
| WO | WO 05/096991 | 10/2005 |
| WO | WO 05/105003 | 11/2005 |
| WO | WO 06/016894 | 2/2006 |
| WO | WO 06/055365 | 5/2006 |
| WO | 2006082586 A2 | 8/2006 |
| WO | 2006127237 A2 | 11/2006 |
| WO | WO 06/127593 | 11/2006 |
| WO | WO 07/041598 | 4/2007 |
| WO | WO 08/030403 | 3/2008 |
| WO | WO 08/033409 | 3/2008 |
| WO | WO 08/033474 | 3/2008 |
| WO | WO 08/141288 | 11/2008 |
| WO | WO 09/011881 | 1/2009 |
| WO | WO 09/011882 | 1/2009 |
| WO | WO 09/086549 | 7/2009 |
| WO | WO 09/117533 | 9/2009 |
| WO | 2009146397 A1 | 12/2009 |
| WO | WO 10/054399 | 5/2010 |
| WO | WO 10/054404 | 5/2010 |

OTHER PUBLICATIONS

International Search Report from PCT Patent Application No. PCT/US2003/004378 dated Aug. 13, 2003.
International Search Report from PCT Patent Application No. PCT/US2003/033605 dated Mar. 29, 2004.
International Search Report from PCT Patent Application No. PCT/US2003/033606 dated Mar. 29, 2004.
International Search Report from PCT Patent Application No. PCT/US2003/004449 dated Aug. 13, 2003.
International Search Report from PCT Patent Application No. PCT/US2004/006695 dated Sep. 8, 2004.
International Search Report from PCT Patent Application No. PCT/US2004/033007 dated Feb. 9, 2005.
International Search Report from PCT Patent Application No. PCT/US2005/014372 dated Jul. 28, 2005.
International Search Report from PCT Patent Application No. PCT/US2006/019727 dated Apr. 19, 2007.
International Search Report from PCT Patent Application No. PCT/US2006/038684 dated Feb. 14, 2007.
International Search Report from PCT Patent Application No. PCT/US2007/019227 dated Feb. 20, 2008.
International Search Report from PCT Patent Application No. PCT/US2007/019833 dated Feb. 20, 2008.
International Search Report from PCT Patent Application No. PCT/US2007/019940 dated Mar. 14, 2008.
International Search Report from PCT Patent Application No. PCT/US2008/008726 dated Oct. 16, 2008.
International Search Report from PCT Patent Application No. PCT/US2008/008729 dated Aug. 18, 2009.
International Search Report from PCT Patent Application No. PCT/US2008/063440 dated Aug. 1, 2008.
International Search Report from PCT Patent Application No. PCT/US2008/088581 dated Feb. 26, 2009.
International Search Report from PCT Patent Application No. PCT/US2009/037586 dated Sep. 28, 2009.
International Search Report from PCT Patent Application No. PCT/US2009/063925 dated Jan. 12, 2010.
International Search Report from PCT Patent Application No. PCT/US2009/063930 dated Jan. 12, 2010.
Felsher, et al., "Mucosal apposition in endoscopic suturing", Gastrointestinal Endoscopy, vol. 58, No. 6, pp. 867-870, (2003).
Stecco, et al., "Trans-oral plication formation and gastric implant placement in a canine model", Stecco Group, San Jose and Barosense, Inc., Redwood City, CA (2004).
Stecco, et al. "Safety of a gastric restrictive implant in a canine model", Stecco group, San Jose amd Barosense, Inc., Redwood City, CA (2004).

\* cited by examiner

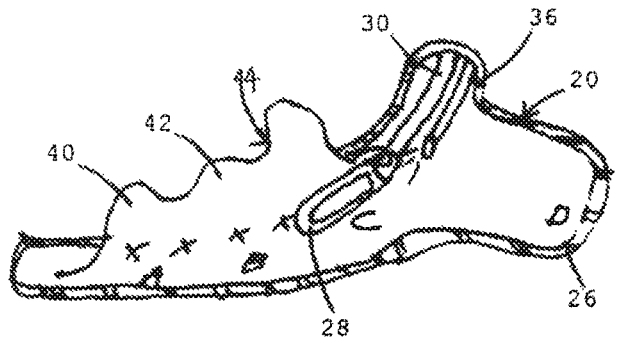
Fig. 1D
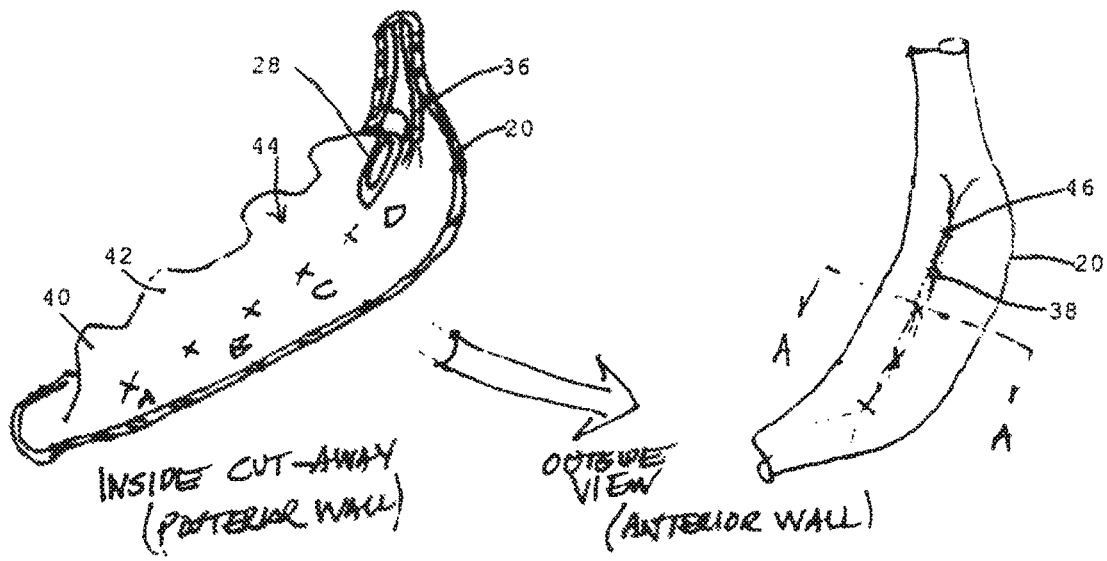
Fig. 1E
Fig. 1F
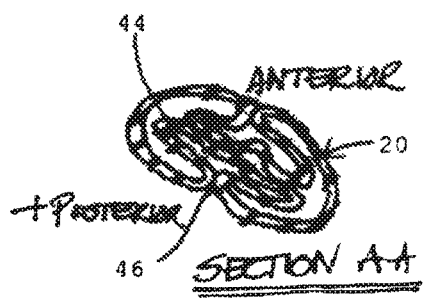
Fig. 1G

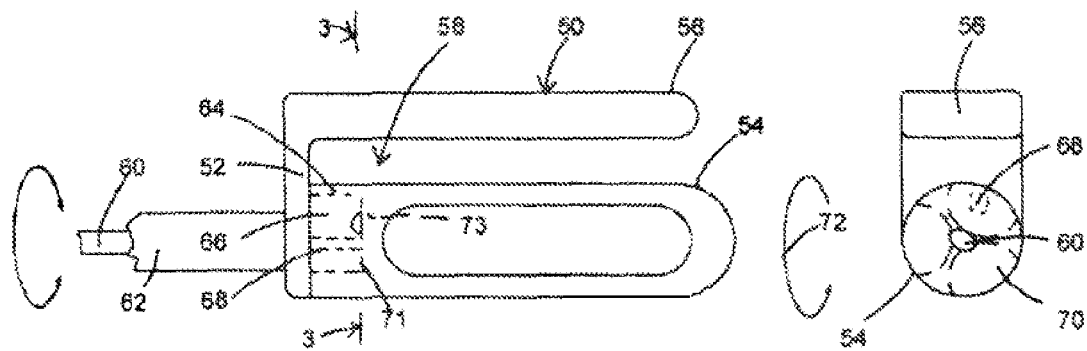
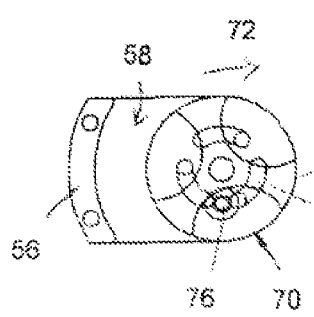
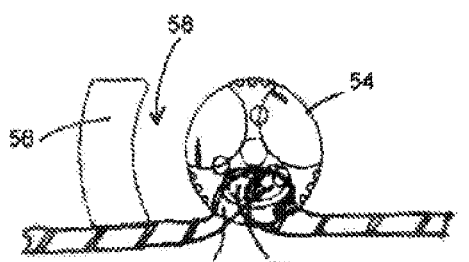
Fig. 2A
Fig. 2B
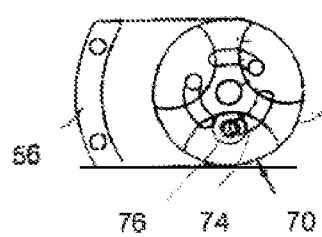
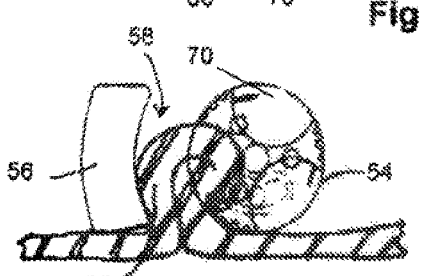
Fig. 4A
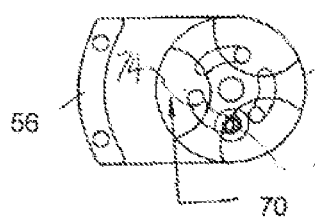
Fig. 4B
Fig. 4C

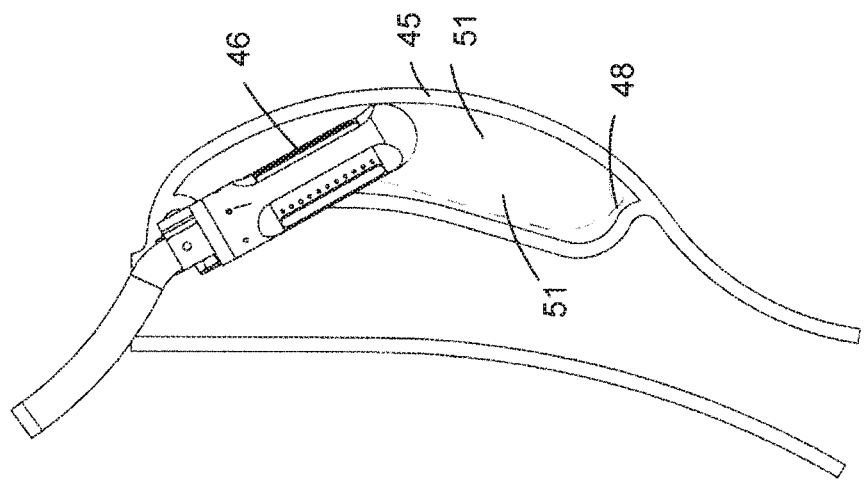
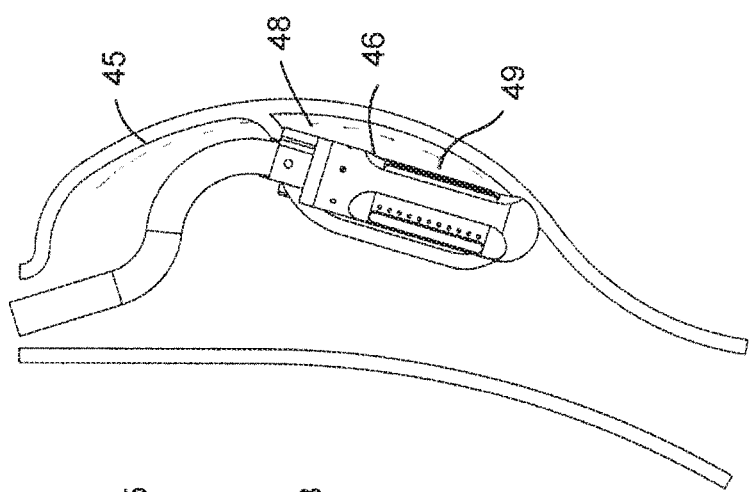
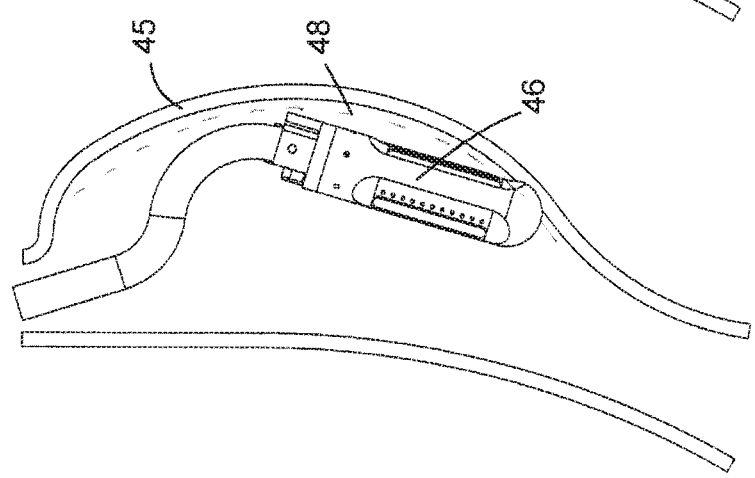
Fig. 10A
Fig. 10B
Fig. 10C

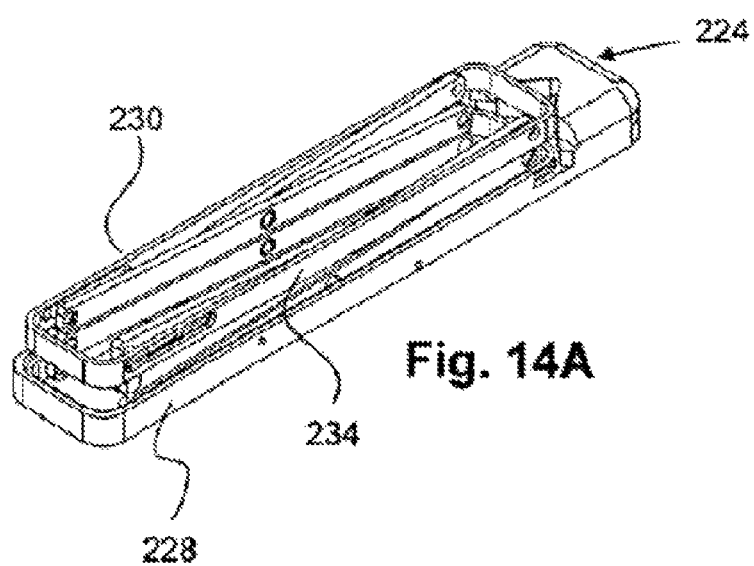

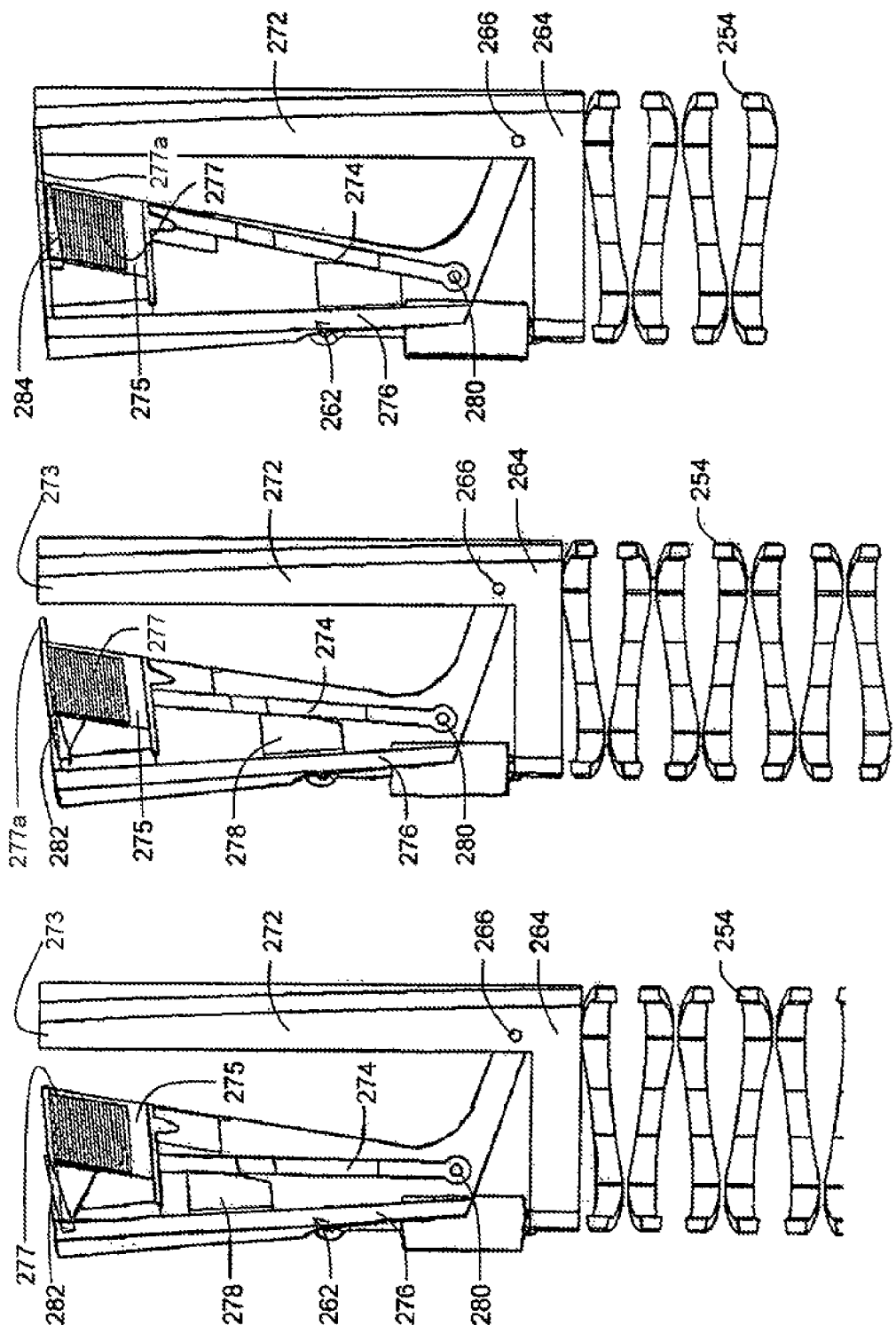

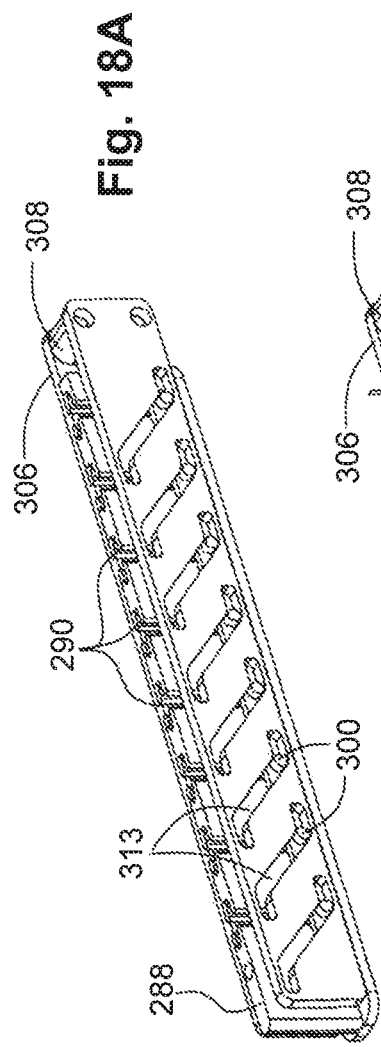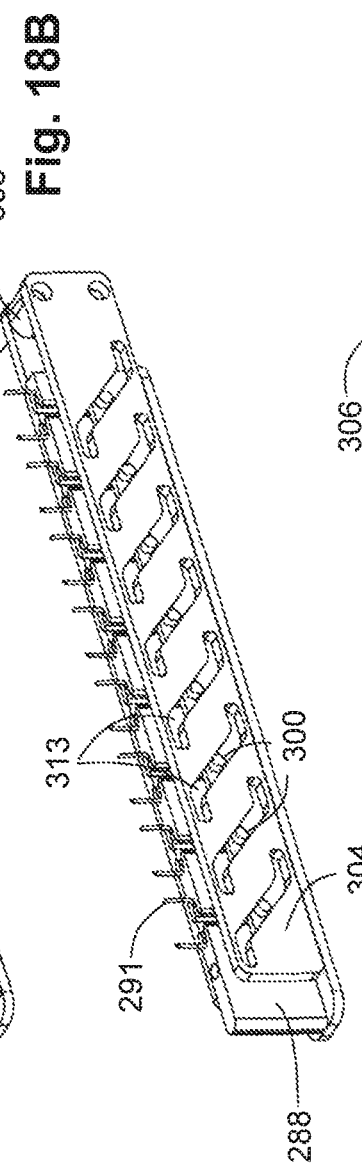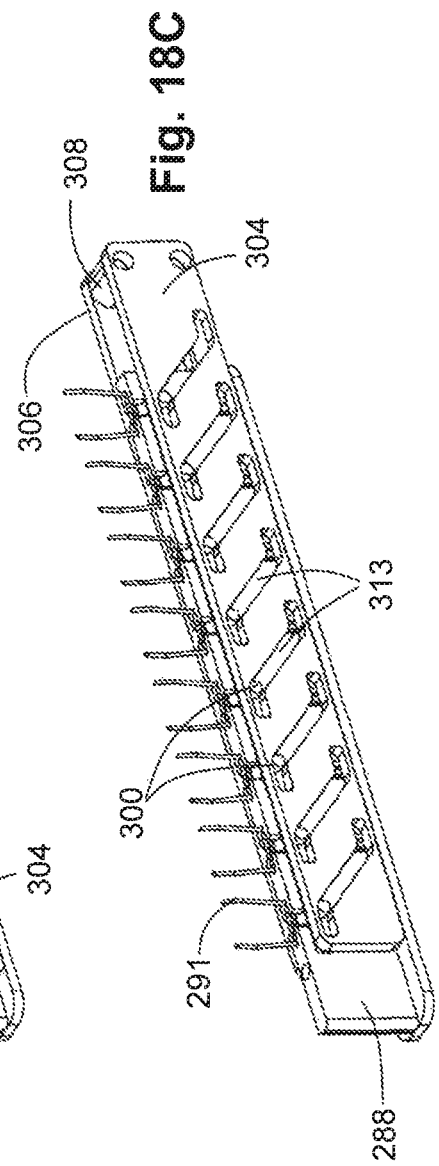

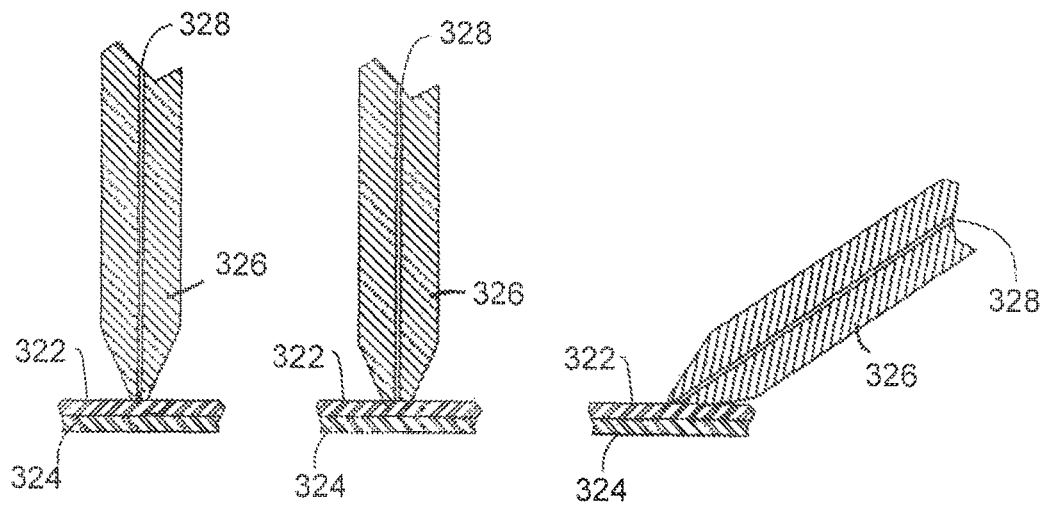
Fig. 19A  Fig. 19B  Fig. 19C
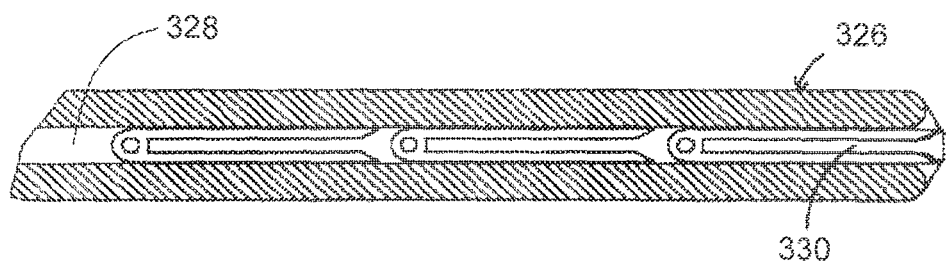
Fig. 20
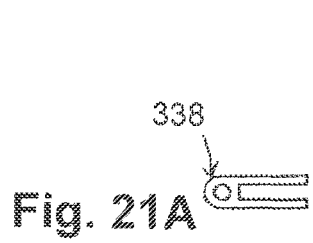
Fig. 21A
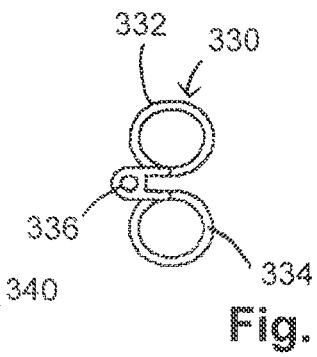
Fig. 21B
Fig. 21C
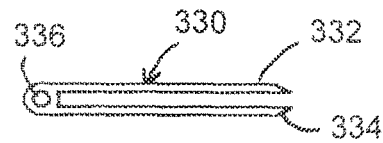
Fig. 21D

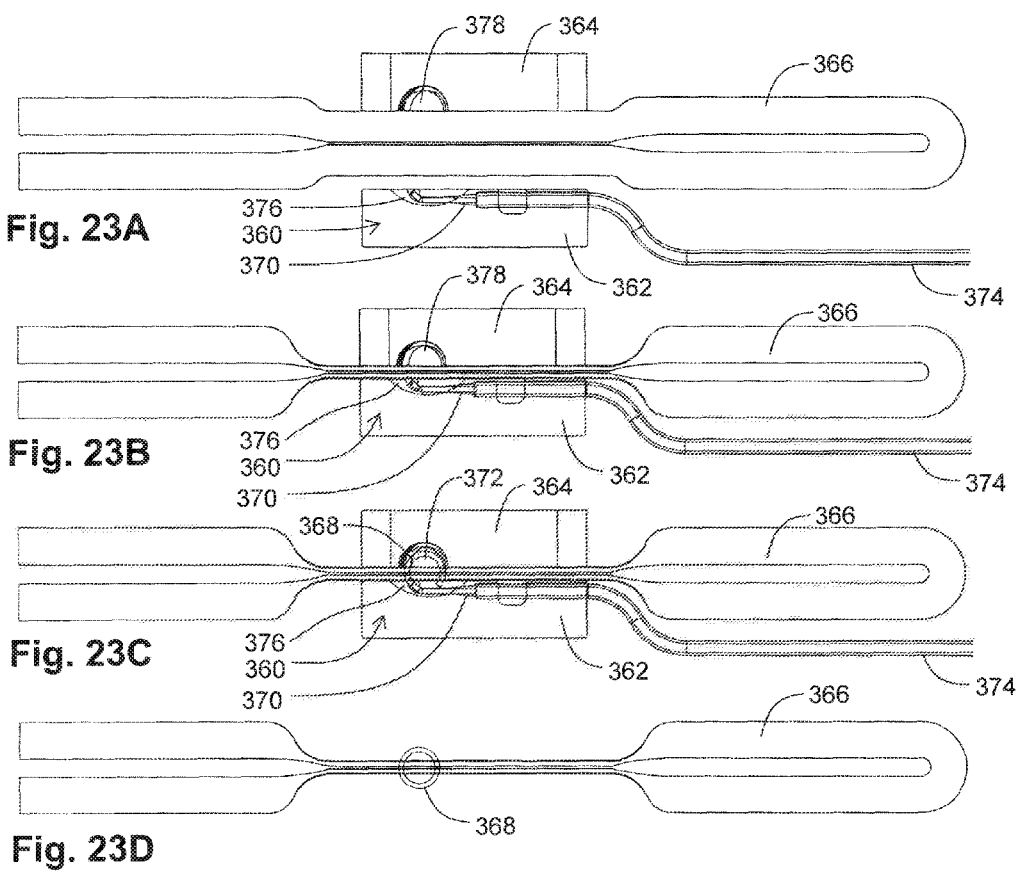

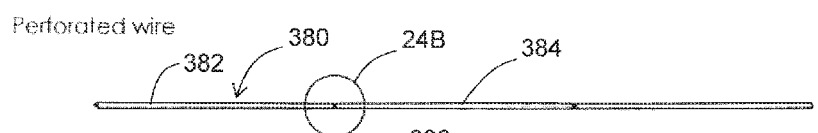
Fig. 24A
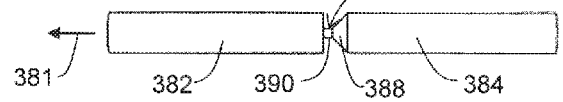
Fig. 24B
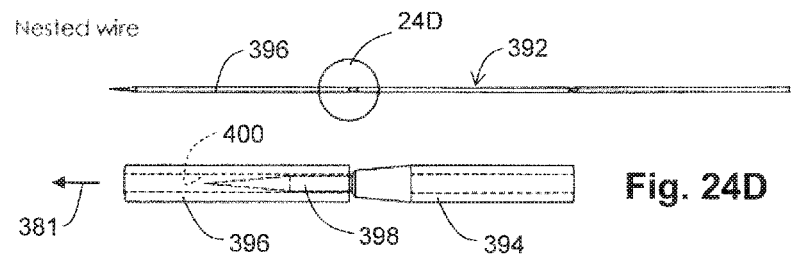
Fig. 24C
Fig. 24D
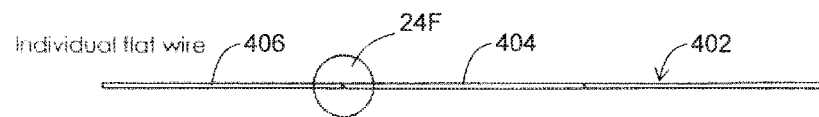
Fig. 24E
Fig. 24F

TISSUE-ACQUISITION AND FASTENING DEVICES AND METHODS

CROSS-REFERENCE TO RELATED APPLICATIONS

This application is a continuation of U.S. application Ser. No. 15/165,425, filed May 26, 2016, which is a continuation of U.S. application Ser. No. 13/112,664, filed May 20, 2011, which claims priority to U.S. Provisional Application No. 61/347,345, filed May 21, 2010, each of which is herein incorporated by reference in its entirety.

FIELD OF THE INVENTION

The present invention relates to devices and methods for acquiring and fastening tissues folds within an internal organ, such as the stomach, and for applying the devices and methods to producing reductions in organ volume or repair of bariatric procedures.

BACKGROUND OF THE INVENTION

Numerous surgical procedures are performed to treat the chronic disease of obesity. Common surgical procedures include Roux en Y gastric bypass, Sleeve Gastrectomy, Gastric Banding and Biliopancreatic Diversion with or without duodenal switch. Each of these are effective in the treatment of obesity, but carry inherent risks associated with surgery, stapling and transection of the stomach, and pain and potential infection(s) associated with post operative recovery due to the skin incisions. Additionally, access to the patient's stomach is difficult in obese patients, further complicating the surgery.

A relatively new surgical procedure has been performed which does not require stapling or transection of the stomach. In this procedure the stomach is exposed, and the greater curvature of the stomach is first freed from any connective tissue or vasculature. The greater curvature of the stomach is then rolled in on itself (Inverted) and sewn together using suture or clips. This process is continued until sufficient folds of tissue have been inverted to produce a reduction in stomach size and also a reduction in the motility of the stomach. The procedure itself is time consuming due to the difficult access, the need to cut away connecting tissue, and the required hand stitching/clipping of the folds, and the patient is subjected to all of the risks of other surgical procedures.

The invention herein reduces these problems by performing a stomach-volume reduction procedure in a completely transoral method, requiring no incisions to reach the site of operation. In this method, a tissue-acquisition device is inserted down the throat and unlike the prior art, large volumes of tissue are able to be acquired and fastened, aligning serosa to serosa. Since the procedure is done transorally, no freeing of connective tissue on the exterior of the stomach is performed. And rather than inverting the greater curvature, plications (inversion of tissue) are performed on the anterior and/or posterior walls and/or fundus to reduce stomach size and motility. These serosal layers are then secured using standard staples, clips, fasteners, or the like.

Methods for carrying out various stomach plication or remodeling procedures transorally are known in the art. U.S. Pat. Nos. 7,204,842, 7,153,314, 6,926,722, 5,887,594, 5,676,674, 5,403,326, and for example, disclose methods and devices for creating folds at or near the gastro-esophageal junction, in the treating of gastroesophageal reflux disease (GERD). U.S. Pat. Nos. 7,175,638, 6,835,200, 6,821,285, 6,494,888, 6,558,400 and 6,086,600 disclose tissue plication methods and device for capturing and fastening individual serosal-to-serosa tissue plications within an internal organ, such as the stomach. U.S. Pat. Nos. 7,288,101, 7,097,650, 7,083,692, 7,306,614, 6,773,441, and 6,663,639 disclose methods and devices for remodeling the stomach by drawing together and fastening a pair of individual tissue plications formed in remote regions of the stomach. However, none of the above references discloses forming elongate, extended serosal-to-serosa tissue folds in the stomach, in the treatment of obesity-related eating disorders, or devices that are designed for efficiently forming such extended folds.

SUMMARY OF THE INVENTION

A. Method of Forming a Continuous, Extended Two-Layer Tissue Fold

The present invention includes, in one aspect, a method of treating an obesity-related eating disorder in a patient, by the steps of: (a) intraorally placing within the patient's stomach, a tissue-acquisition device capable of acquiring and fastening a laterally extending two-layer tissue fold; (b) placing the tissue-acquisition device against a selected region of the interior of the stomach's anterior wall, posterior wall, or fundus; (c) operating the device to acquire and fasten a laterally extending two-layer tissue fold; (d) moving the tissue-acquisition to place it against a new selected interior stomach region adjacent the fastened tissue fold formed in step (c), such that the device, when operated to acquire a tissue fold, will form a single laterally extending tissue fold that includes the fold formed in step (c) and which extends along a region of the stomach's anterior wall, or posterior wall, or fundus; and (e) repeating steps (c) and (d) until an elongate, continuous two-layer tissue fold composed of at least three individually-fastened folds formed in steps (c) is formed in the stomach's anterior wall, posterior wall, or fundus.

Step (e) of the method may be carried out until the total volume of the stomach interior has been reduced by at least 40%, and/or until a length of tissue fold effective to substantially reduce stomach motility, as evidenced by a reduction in measured periodic motor activity after eating, is created.

In one embodiment, the tissue-acquisition device used to acquire and fasten tissue in step (c) includes an open-end roller device having a roller, a roller-confronting arm, and a clamping mechanism activatable to move the arm between open and closed conditions; where step (c) includes rotating the roller in a direction effective to draw a tissue fold between the roller and arm, and step (d) includes activating the clamping mechanism to its open and closed positions, respectively, before and after moving the device to a position in which the open end of the device embraces a region of a previously acquired and fastened tissue fold. The roller in the device may have a plurality of elongate tissue-capture chambers distributed radially about the roller, such that applying a vacuum to the roller while rotating the roller in the tissue-advancing direction functions to draw a tissue fold between the roller and arm by successive capture and release of tissue in successive tissue-capture chambers. The device may further include a pusher operable to eject a fastener through a tissue fold formed between the roller and arm of the device; and step (c) includes activating the pusher to place a fastener between the layers of a tissue fold.

In another embodiment, the tissue-acquisition device used to acquire and fasten tissue includes an auger-blade tissue-acquisition device having (i) a frame, (ii) a pair of interleaved, helical-surface augur blades that are mounted on the frame for rotation about substantially parallel axes and for movement toward and away from one another under a force that biases the two blades toward one another, and (iii) a drive mechanism for rotating at least one of the two blades in a selected direction.

In a third embodiment of the method, the tissue-acquisition device used to acquire and fasten tissue in step (c) includes a scissor-arm cage covered by a flexible membrane that is open at one side of the cage only; the cage is expandable from a collapsed condition for step (a) to an expanded condition operable to draw a two-layer tissue fold into the cage, when the cage's open side is placed against a selected stomach region in steps (b) or (d), and a vacuum is applied to the interior of the cage in step (c).

In each of these embodiments, the tissue-acquisition device may have a fastener mechanism for fastening tissue folds integrated into the device, or a fastening mechanism that operates independently of the structure used in for tissue acquisition. Suitable fastener mechanisms that can either be integrated into a tissue-acquisition device or operated independently are described below in Sections G-J.

B. Method of Restoring a Vertical Sleeve Gastrectomy

In a related aspect, the invention includes a method of restoring a vertical sleeve gastrectomy (VSG) procedure that has failed in a patient because the patient's stomach has expanded and regained a significant portion of its pre-surgical volume, by incorporating the vertical stomach seam formed in the initial VSG operation into an elongate fold in the stomach, by the steps of: (a) intraorally placing within the patient's stomach, a tissue-acquisition device capable of acquiring a two-layer tissue fold by vacuum and fastening the fold to form a plication; (b) placing the tissue-acquisition device against a region of the stomach adjacent the seam formed during the vertical sleeve gastrectomy; (c) operating the device to acquire and fasten a two-layer tissue fold that contains a section of the VSG seam, (d) moving the tissue-acquisition to place it against a new selected interior stomach region adjacent the fastened tissue fold formed in step (c), and (e) repeating steps (c) and (d) until the VSG volume of the stomach has been restored.

Any of the devices described in Sections C-F below may be used in practicing the method. In a preferred embodiment, the method is carried out, as in Section A, to form a single continuous, extended plication that incorporates the VSG seam, employing one of the tissue-acquisition device described in Section C-E.

C. Roller-Arm Tissue-Acquisition Device and Method

The invention further includes a roller-arm tissue-acquisition device for acquiring a tissue fold. The device has (i) a support frame, (ii) an elongate roller mounted on the frame for rotation about the roller's long axis, where the roller includes tissue-engaging structure for engaging tissue and advancing the engaged tissue in the direction of roller rotation; (iii) a roller driver for rotating the roller in a tissue-advancing direction; (iv) an arm mounted on said frame at a position spaced from and confronting the roller, between which a two-layer tissue fold is formed, as tissue is advanced into and through the device as the roller is rotated; and (v) a vacuum conduit in the frame for connecting an external vacuum source to said roller or to the arm, to hold one layer of a two-layer tissue fold by vacuum adherence, as tissue is being advanced into and through the device by rotation of the roller.

For use in forming a tissue fold in within the interior of the gastrointestinal tract, the device further includes an elongate shaft having a distal end at which the device frame is attached and a proximal end having user controls by which a user can control the operation of the device outside the patient's body after intraoral placement of the device within the patient's gastrointestinal tract.

The tissue engaging structure in the roller may include a plurality of elongate tissue-capture chambers formed in the roller and distributed radially about the roller, where the vacuum conduits are operable to connect an external vacuum source to successive capture chambers as the roller is rotated, in a tissue-advancing direction, such that a tissue fold tissue is drawn into and through said device by successive capture and release of tissue in successive tissue-capture chambers.

The frame in the device may include a post on which the roller is rotatably mounted about an axis. The post has a fixed plate with a vacuum port in the vacuum conduit that is offset from the axis. The roller may include a rotatable plate that confronts and contacts the fixed plate when the roller is rotated. The rotatable plate may include a plurality of elongate, recesses in the vacuum conduit, each of which moves in an out of fluid communication with the vacuum port in the first plate as the roller is rotated, to successively communicate each tissue-capture chambers in the roller with the vacuum port through the associated elongated recess in the roller plate.

The device is preferably open at one end, and may further include a clamping mechanism activatable to move the arm between an open position in which the arm and roller can embrace a side region of an already formed tissue fold and a closed condition in which a tissue fold can be formed in the device by rotating the roller. The arm may itself include a roller mounted thereon for rotation about the arm's long axis.

The device may further include a fastener mechanism operable to eject a fastener through a tissue fold captured between the roller and support arm of the device, where one of the roller and arm is adapted to carry and eject one or more fasteners. The fastener mechanism may include an elongate slot defined in said arm and adapted to hold in-line, a plurality of U-shaped fasteners, each preformed to adopt the shape of a two-loop fastener when the fastener is ejected from the slot, and a pusher for ejecting individual fasteners from the slot. In another embodiment, the fastener mechanism may include an elongate tube through which a metal wire can be advanced, a distal end deflection member, and a pusher for an advancing such a wire within the tube against the deflection member, wherein the wire is coiled as it exits the tube to form a coiled-wire fastener that fastens a tissue fold formed in the device.

The device is designed for use in a method of acquiring a tissue fold in a body tissue or organ, by the steps of: (a) positioning against the body tissue or organ, an opposed-roller tissue-acquisition device of the type described, (b) applying a vacuum to the roller or arm of the device to adhere one of the two tissue layers of a tissue fold, as tissue is advanced between the roller and arm; (c) while applying said vacuum, engaging the drive mechanism to rotate the roller in a direction that advances tissue between the roller and arm; (d) continuing the rotating until a desired-size tissue fold has been formed between the roller and arm; (e) fastening the fold; and (f) releasing the fastened fold from the device. Fastening step (e) may include ejecting a fastener through the fold from the arm or roller.

For use in acquiring a tissue fold within the stomach, positioning step (a) may include introducing the device into the stomach intraorally and employing an endoscope to position the device against a selected region of the stomach where it is desired to form the tissue fold.

For use in forming an extended, continuous two-layer tissue fold within the stomach, steps (a)-(e) may be repeated at each of a plurality of locations along a preselected tissue-fold line within the stomach, so as to form an elongate, continuous two-layer tissue fold composed of at least three individually-fastened folds formed in steps (a)-(e).

Where the tissue-acquisition device is open at one end, positioning step (a) may include moving the device to a position in which the open end of the device embraces a side portion of a previously acquired and fastened tissue fold.

D. Auger-Blade Tissue-Acquisition Device and Method

Also disclosed is an auger-blade tissue-acquisition device for acquiring a tissue fold. The device includes (i) a frame, (ii) a pair of helical-surface augur blades that are mounted on the frame for rotation about substantially parallel axes and for movement toward and away from one another under a force that biases the two blades toward one another, and (iii) a drive mechanism for rotating at least one of the two blades in a selected direction.

Each auger blade may have a proximal section of relatively low pitch, a distal section of relatively high pitch, and a center region of intermediate pitch, where the width of the each blade in the proximal section is tapered on progressing toward the proximal end of the blade. The two blades are mounted for rotation on a pair of bases, and these bases are adapted to move toward and away from one another, under a biasing force, allowing the blades to accommodate tissue material as is acquired between the blades, while maintaining the tissue under a moderate compression force.

For use in forming a tissue fold in within the interior of the gastrointestinal tract, the device further includes an elongate shaft having a distal end at which the device is attached and a proximal end having user controls by which a user can control the operation of the device outside the patient's body after intraoral placement of the device within the patient's gastrointestinal tract.

The device may further include a fastener mechanism for ejecting a fastener through a tissue fold formed by the device. One such fastener includes a conduit through which a plurality of pre-formed metal-wire segments can be advanced, and a pusher which is operable to advance the segments within the conduit, where the wire assumes a coiled configuration as it exits the tube to form a coiled-wire fastener effective to fasten a tissue fold formed in the device.

The auger-blade device is designed for use in a method of acquiring a tissue fold in a body tissue or organ, by the steps of: (a) positioning against the body tissue or organ, an auger-blade tissue-acquisition device of the type described above, (b) activating the drive mechanism, causing tissue to be drawn between the two blades, thus forming a tissue fold; (c) fastening the tissue fold formed between the two blades; and (d) releasing the device from the fold by reversing the direction of blade rotation.

For use in acquiring a tissue fold within the stomach, positioning step (a) may include introducing the device into the stomach intraorally, with the blades in their tissue-capture condition, and employing an endoscope to position the device against a selected region of the stomach where it is desired to form the tissue fold.

For use in forming an extended, continuous two-layer tissue fold within the stomach, steps (a)-(d) may be repeated at each of a plurality of locations along a preselected tissue-fold line within the stomach, so as to form an elongate, continuous two-layer tissue fold composed of at least three individually-fastened folds formed in steps (a)-(d).

E. Scissor-Arm Cage Tissue-Acquisition Device and Method

In another aspect, the invention includes a scissor-arm tissue-acquisition device for acquiring and fastening a tissue fold. The device has (i) a scissor-arm cage having an opening on one side thereof; (ii) a flexible membrane covering said cage and optionally, a portion of said opening; (iii) an drive mechanism for expanding the cage from a low-profile, collapsed-arm condition to an expanded-arm condition in which the cage defines a tissue-capture chamber covered by the membrane, and (iv) a vacuum port through which vacuum can be supplied to the tissue-capture chamber, with the cage in its expanded-arm condition, to draw a tissue fold into the chamber through said opening. The device may further include a fastener mechanism, such as a linear stapler, or clip-fastener or coiled-wire fastener of the types described below.

For use in forming a tissue fold in within the interior of the gastrointestinal tract, the device may further include an elongate shaft having a distal end at which the device is attached and a proximal end having user controls by which a user can control the operation of the device outside the patient's body after intraoral placement of the device within the patient's gastrointestinal tract.

The device is designed for use in a method of acquiring a tissue fold in a body tissue or organ, by the steps of (a) positioning against the body tissue or organ, a scissor-arm tissue-acquisition device of the type described above, (b) with the cage in its expanded-arm condition, and the opening placed against the body tissue or organ, applying vacuum to the cage, causing tissue to be drawn into the cage, thus forming a tissue fold; (c) fastening the tissue fold formed within the cage; and (d) releasing the fold from the device by releasing the vacuum applied to the cage.

For acquiring a tissue fold within the stomach, the positioning step may include introducing the device into the stomach intraorally, with the cage in its collapsed-arm condition, and employing an endoscope to position the device against a selected region of the stomach where it is desired to form the tissue fold.

For use in forming an extended, continuous two-layer tissue fold within the stomach, steps (a)-(d) may be repeated at each of a plurality of locations along a preselected tissue-fold line within the stomach, so as to form an elongate, continuous two-layer tissue fold composed of at least three individually-fastened folds formed in steps (a)-(d).

F. Hollow Tube Tissue-Acquisition Device and Method

In another aspect, the invention includes a hollow-tube tissue-acquisition device for acquiring and fastening a tissue fold. The device includes (i) an elongate hollow tube into which tissue can be drawn with application of a vacuum to the tube and (ii) stapler head carried at the distal end of the tube, and movable between an open condition defining a chamber through which tissue can be drawn into the tube, and a closed condition in which a stapler assembly in the stapler head can be operated to fasten a tissue fold drawn into the tube.

For use in forming a tissue fold in within the interior of the gastrointestinal tract, the device further includes an elongate shaft having a distal end at which the device is attached and a proximal end having user controls by which a user can control the operation of the device outside the patient's body after intraoral placement of the device within the patient's gastrointestinal tract.

The stapler assembly in the stapler head may be constructed to hold a plurality of stacked staples, and include a staple ejector for ejecting individual staples from the assembly, where the head also includes an anvil frame on which the stapler assembly is pivotally mounted and which provides an anvil surface for crimping staples ejected from the stapler assembly. Alternatively, the stapler head may include an elongate slot adapted to hold in-line, a plurality of U-shaped fasteners each preformed to adopt the shape of a two-loop fastener when the fastener is ejected from the slot, and said pusher is operable to eject individual fasteners from the slot. In still another embodiment, the stapler head may include an elongate tube through which a metal wire can be advanced, a distal end deflection member, and said pusher is operable to advance such a wire within the tube against the deflection member, wherein the wire is coiled as it exits the tube to form a coiled-wire fastener effective to fasten a tissue fold formed in the device.

The tube acquisition device is designed for use in a method acquiring a tissue fold in a body tissue or organ, by the steps of (a) positioning against the body tissue or organ, a hollow-tube tissue-acquisition device of the type described, (b) activating the stapler head to place the chamber defined by the head in its open condition; (c) applying a vacuum to the device, to draw tissue through the chamber into the tube, thereby to form a tissue fold; (d) fastening the tissue fold, and (e) releasing the fastened fold from the device.

For acquiring a tissue fold within the stomach, the position step (a) may include introducing the device into the stomach intraorally, with the device in its closed, low-profile condition, and employing an endoscope to position the device against a selected region of the stomach where it is desired to form the tissue fold.

For use in forming an extended, continuous two-layer tissue fold within the stomach, steps (a)-(e) in the method may be repeated at each of a plurality of locations along a preselected tissue-fold line within the stomach, so as to form an elongate, continuous two-layer tissue fold composed of at least three individually-fastened folds formed in steps (a)-(e).

G. Linear Stapler Device

In still another aspect, the invention includes a stapling device for applying a linear array of staples to a tissue. The device includes (i) a housing; (ii) a staple cartridge contained within said housing for holding a plurality of staples in a linear array; (ii) a pusher assembly having a plurality of pusher surfaces arrayed to simultaneously engage respective staples held in said cartridge, to eject the staples from the cartridge as the pusher assembly moves in a bottom-to-top direction within the housing between lowered and raised positions, and a linear array of pins extending along at least one side of the pusher assembly; (iii) an ejector assembly having at least one drive plate disposed within said housing for movement in an end-to-end direction between load and retracted positions, where the drive plate has a linear array of angled slots formed in a side thereof, and in which pins in the pusher assembly ride, such that movement of the drive plate from its initial load toward its retracted position forces the pusher assembly from its lowered to its raised condition; and (iv) an anvil disposed adjacent the top surface of the housing, for crimping staples ejected from the cartridge when the drive plate is moved from its load to its retracted position.

H. Clip Fastener Device

Also disclosed is a multi-fire fastener device for fastening two or more layers of material together. This device has (i) an arm, (ii) an elongate slot formed in the arm, (iii) disposed in the slot, one or more U-shaped fasteners, each having a pair of elongate, side-by-side legs that are preformed to adopt the shape of a loops when the fastener is ejected from the slot, and (iv) a pusher for ejecting individual fasteners from the slot.

The slot in the device may have a trapezoidal cross-sectional shape and a length dimensioned to accommodate a plurality of fasteners arranged inline.

The fasteners may be composed of a titanium-containing alloy such as nitinol, and may be formed by laser-cutting a titanium-alloy tube having a thickness between 2 and 20 mils, and an inner diameter between 60-120 mils.

I. Coiled-Wire Fastener Device

In a further aspect, the invention includes a coiled-wire multi-fire fastener device for fastening two or more layers of material together. The device has (i) a hollow feed tube; (ii) a wire dimensioned for linear advancement within said tube, where in one embodiment, the wire has a plurality of coil segments interspersed with breakaway segments designed to break when the wire is subject to a selected bending force, (iii) a deflection member carried at the distal end of the tube for bending a coiled segment of the wire into a coil, as the distal end portion of the wire is advanced out of the feed tube, where each coil segment is dimensioned to form at least a full-circle coil before the next-in-line breakaway segment is bent and breaks as it passes over the deflection member, and (iv) a pusher for advancing the wire within the tube.

The breakaway segments of the wire may be tapered in wire diameter on progressing in a distal direction, such that the region of greatest susceptibility to breaking is the interface between a coil segment and its trailing breakaway segment, such that each successive coil segment has a tapered-diameter end as it is advanced out of the tube.

The device may further include an anvil having a curved deflection surface.

J. Barbed-Anchor Fastener Device

Also forming part of the invention is multi-fire barbed-anchor fastening device for fastening two or more layers of material together. The device includes a distal-end clamp having first and second clamping arms that can be moved toward and away from a closed, clamping condition, and first and second anchor tubes that terminate distally adjacent the distal ends of the first and second clamping arms, respectively. Carried in the first anchor channel is a linear string of first anchor components, each having a barb that is held in a retracted nested position within its tube and which is based to swing outwardly when moved out of its anchor channel. Carried in the second anchor channel, a linear string of second anchor components, each having a socket to receiving such first anchor-component barb, when the two anchor components are pressed together, to form a locked anchor. First and second pushers in the device functions to advance the first and second anchor members, respectively, to load a distal-most anchor member at the distal end of the associated clamping arm. A clamping mechanism in the device is activatable to move the clamping arms, with such loaded with first and second anchor members, toward their closed, clamping condition, to fasten a tissue fold held between the two arms.

These and other objects and features of the invention will become more fully apparent when the following detailed description of the invention is read in conjunction with the accompanying drawings.

BRIEF DESCRIPTION OF THE DRAWINGS

FIGS. 1A-1G illustrate various views of a patient stomach during an operation in accordance with an aspect of the invention for reducing stomach volume;

FIGS. 2A and 2B are simplified side and front-on views of a roller-arm tissue-acquisition device constructed in accordance with one embodiment of the invention;

FIGS. 3A-3D are sectional views taken through line 3-3 in FIG. 2A, showing successive rotational position of a roller in the device;

FIGS. 4A-4C are head-on views of the device in FIG. 2A, showing successive capture and release of tissue during formation of a tissue fold in the device;

FIGS. 10A-10C illustrate the method for repairing a vertical sleeve gastrectomy (VSG) in a patient, in accordance with an aspect of the invention;

FIGS. 14A and 14B illustrate a scissor-arm tissue-acquisition device formed in still another aspect of the invention, shown in closed (FIG. 14A) and expanded (FIG. 14B) conditions;

FIG. 16A-16C illustrate the operation of the stapling mechanism in the hollow-tube tissue-acquisition device;

FIGS. 18A-18C illustrate three operational positions of the linear stapler device of FIG. 17 in ejecting a linear array of staples;

FIGS. 19A-19C illustrates the fastening of a two-layer fold with a preformed fastener, under various conditions;

FIG. 20 shows fasteners in a slot formed in the arm or holder of a tissue-acquisition device;

FIGS. 21A-21D show various types of two-arm fasteners before and after ejection from a fastener holder;

FIGS. 23A-23D illustrate in side sectional views, a coil-wire fastener device in an open, tissue-acquisition condition (23A), in an initial tissue fastening condition (23B), just before completion of the fastening operation (23C); and just after the wire in the device breaks at its distal end (FIG. 23D);

FIGS. 24A-24F are side views of three different embodiments of a wire used in the coil-wire device in FIG. 23, where FIGS. 24B, 24D, and 24F are enlarged views of the circled regions in FIGS. 24A, 24C, and 24E, respectively.

DETAILED DESCRIPTION OF THE INVENTION

A. Method of Stomach Volume Reduction

In accordance with one aspect, there is provided a method for treating an obesity-related eating disorder in a patient by creating, an elongate continuous tissue plication in the anterior wall, posterior wall, and/or fundus of a patient's stomach. The terms "tissue plication" and "tissue fold" are used interchangeably herein, and as applied to the present method, refer to a two-layer tissue fold within the stomach having an serosal surfaces in contact with one another.

The method preferably employs tissue-acquisition devices and methods which will be detailed below in Sections C-E. For purposes of this section, it is worth noting only that a device suitable for the method (i) can be placed within the stomach intraorally at the distal end of a flexible shaft also having user controls at its proximal end, (ii) includes tissue-acquisition structure for capturing and fastening a two-layer tissue plication within the stomach, and (iii) can be moved along a linear region with the anterior or posterior wall and/or fundus to successively capture and fasten adjacent tissue regions, to form a single laterally extending tissue fold that includes at least three individually-fastened folds or plications.

Figure 1A:
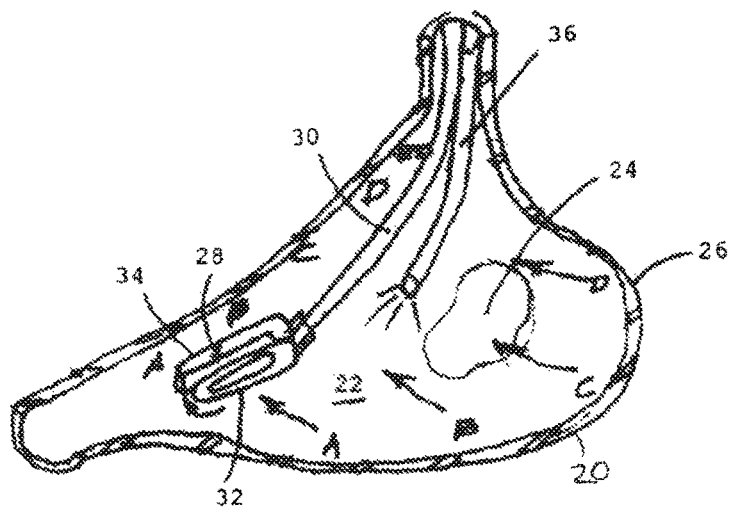

The method is illustrated in FIGS. 1A-1G, where a patient's stomach 20 is shown in sectional view approximately midway between the dorsal (back) wall 22 and the ventral (front) wall, shown fragmentarily at 24 in FIG. 1A. The fundus at the top of the stomach is shown at 26. A tissue-acquisition and fastening device 28 is carried at the distal end of a flexible shaft 30 which is dimensioned to allow intraoral access to preferably the entire stomach from a user position outside the patient's mouth. For simplicity, the tissue acquisition device is shown in the figures simply as two confronting members 32, 34 between which a tissue fold is to be acquired, as seen best in FIGS. 1A and 1B. In certain roller-arm embodiments of a tissue-acquisition device, described in Section C below, the two members include a roller and confronting arm, where a vacuum is applied to one of the two members while the roller functions to feed a tissue fold between the two members.

Although not shown, the proximal end of shaft 30 has controls by which the physician can manipulate the operation of the device. As will become apparent, the user controls allow control of the position of the device in the stomach, the operation of the device in acquiring a stomach plication in the anterior wall, posterior wall and/or fundus in the stomach, the operation of the device in fastening the just-acquired plication, and the operation of the device in advancing to an adjacent region and extending the plication. Also shown in the figures is an endoscope 36 by which the user can view and guide the just-described operations.

Figure 1B:
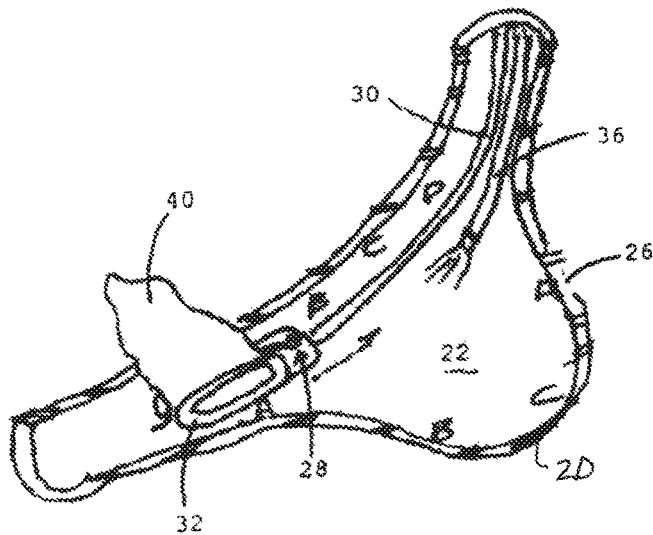
Figure 1C:
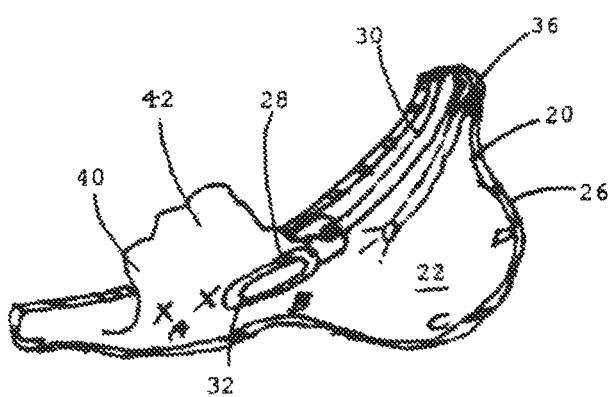

After introducing the tissue-acquisition device into the patient's stomach, the physician places the device against a selected interior region of the stomach anterior wall 24, posterior wall 22, or fundus, as shown in FIG. 1A. In a preferred embodiment, the physician plans and selects a fold line along one or more of these stomach surfaces along which an extended fold will be formed, and places device 28 at one end of the planned fold line, preferably the most distal point along the fold line, as indicated in FIGS. 1A and 1B. Next, the physician operates the device to acquire a serosa-to-serosa laterally-extending tissue fold or plication, such as fold 40 in FIG. 1B, and fastens the fold, as detailed below. As the term is used herein, a "laterally-extending tissue plication" refers to a tissue plication having a two-layer planar expanse whose height, above the base of the plication, is smallest at the upstream and downstream ends of the plication, such as upstream and downstream ends 40a and 40b, respectively in plication 40 in FIG. 1B, and greatest at one or more interior regions of the fold, indicated at 40c in FIG. 1B.

Once a first laterally-extending tissue plication is formed, the device is moved to place it against a new selected interior stomach region adjacent the fastened tissue fold just formed, such that the device, when operated to acquire a tissue fold, will form a new tissue plication whose "upstream" planar expanse portion overlaps with a "downstream" planar expanse portion of the newly formed plication, to form a single laterally-extending tissue fold that includes the new fold and the previously formed fold. This operation can be seen in FIG. 1C, which shows new fold 42 formed adjacent fold 40, the two folds forming a single laterally extending tissue plication. These steps are repeated one or more times, as illustrated in FIGS. 1D and 1E, until an elongate, continuous two-layer tissue fold 44 composed of at least three individually-fastened folds, such as folds 40, 42, is formed in the stomach's anterior wall, posterior wall, or fundus. FIG. 1F shows an exterior tissue-fold line 46 as would be seen from the exterior surface of the stomach, recognizing that this fold line is not visible to the physician. As noted above, this fold line may be formed along the anterior wall, posterior wall, and/or fundus of the stomach.

FIG. 1G shows a cross-section of the stomach taken through a plication region of the stomach along view line A-A in FIG. 1F. As seen, the operation results in a relatively large mass of stomach tissue in the form of an extended fold 44 being taken into the stomach. The operation thus reduces stomach volume in two ways, by reducing the total outer surface area of the stomach (which in turn, defines the internal volume capacity of the stomach) and by filling the internal volume with a relatively large tissue-fold mass. In a preferred embodiment, the total volume of the stomach, that is, the internal volume capable of receiving food, has been reduced by at least 25%, and as much as 40% or more, e.g., up to 60-80% of the original stomach volume. If necessary, the operation is performed along two of more of the target stomach areas (the anterior wall, posterior wall and fundus) to achieve desired large volume reductions.

In addition to the ability to significantly reduce stomach volume, a related embodiment of the method is carried out until there is formed a continuous length of tissue fold effective to substantially reduce stomach motility, as evidenced by a reduction in measured periodic motor activity after eating.

As will be detailed below, the tissue-acquisition device may be open at one end, such that in acquiring an adjacent tissue fold, the device can be moved to a position in which the open end of the device embraces an adjacent side portion of a previously acquired and fastened tissue fold.

The tissue-acquisition device may include an elongate roller, a roller-confronting arm, and an arm-positioning mechanism activatable to move the arm between open and closed conditions, as described above and detailed in Section C. In other embodiments, the tissue acquisition device includes an auger-blade acquisition device (Section D), and a scissor-arm acquisition device (Section E.) As will be seen, all three of these embodiments can be operated to form a series of overlapping plications in which a downstream portion of one plication becomes the upstream portion of the next-in-line plication, resulting in a continuous, extended tissue plication that is fastened along its length at the base of the plication.

B. Method of Restoring a Vertical Sleeve Gastrectomy

A Vertical Sleeve Gastrectomy (VSG) procedure is a common procedure for treatment of obesity. This procedure generates weight loss solely through reduced stomach volume. In the procedure, the stomach is restricted by stapling and dividing it vertically and removing more than 85% of it. The portion of the stomach that remains is shaped like a banana and measures from 1-5 ounces (30-150 cc), depending on the specifics of the operation 7. The nerves to the stomach and the outlet valve (pylorus) remain intact with the idea of preserving the functions of the stomach while drastically reducing the volume. An advantage of the procedure is that there is no intestinal bypass, avoiding the potentially costly, long term complications such as marginal ulcers, vitamin deficiencies and intestinal obstructions.

Over time, the patient's stomach may expand, and ultimately, and as the stomach regains greater volume, the value of the operation in limiting food intake is diminished. A post-surgical stomach with much of its original volume regained is illustrated in FIG. 10A. The present invention provides a simple procedure for restoring the reduced stomach volume of the original procedure, that is, restoring the original VSG stomach volume.

In the procedure, a surgeon initially places a tissue acquisition and fastening device, such as device 46, within the patient's stomach 45, by intraoral introduction. An exemplary device suitable for the method is detailed in Sections C-F below. The tissue-acquisition device is placed near the stomach-tissue seam 48 formed during the vertical sleeve gastrectomy, and typically near the lower end of the seam. The device is now operated to acquire and fasten a two-layer tissue fold 49 that includes a portion of the original VSG seam, as shown in FIG. 10B. The device is now moved to place it against an adjacent stomach region, such that the device, when operated to acquire a tissue fold, will form a plication that contains another section of the VSG seam. These steps are repeated along a length of the stomach until the original VSG volume of the stomach is largely restored. The method is designed to restore stomach volume to close to its original post-VSG volume, as seen in FIG. 10C. Additionally, the elongate plication 51 formed in the method incorporates the VSG vertical seam 48, reducing the risk of infection or tearing of the seam as internal pressure is applied to the seam. In a preferred embodiment of the method, plication 51 is a continuous laterally extending fold of the type formed in the method described in Section A.

C. Roller-Arm Tissue Acquisition Device and Method

In another aspect, the invention includes a tissue-acquisition device for acquiring a tissue fold or plication. The device includes, in operative condition, a support frame; an elongate roller mounted on the frame for rotation about the roller's long axis; an arm mounted on the frame at a position spaced from and confronting the roller, between which a two-layer tissue fold is formed, and a roller driver. The roller includes tissue-engaging structure for engaging tissue and advancing the engaged tissue in the direction of roller rotation. A vacuum conduit in the frame connects an external vacuum source to the roller or arm, to hold one layer of a two-layer tissue fold by vacuum adherence, as tissue is being advanced into and through the device by rotation of the roller.

FIG. 2A is a simplified, side view of a tissue-acquisition device 50 constructed in accordance with one embodiment of the invention. The device include a frame 52, a roller 54 which is mounted on the frame for rotation thereon, about the roller axis, and an arm 56 which confronts the roller and defines therewith, a tissue gap 58 in which a tissue fold is acquired. The roller includes tissue engaging structure (described below) for engaging tissue being acquired and can be rotated in a selected rotational direction by an external or internal roller driver. In the embodiment shown, the driver includes an external mechanism, such as a motorized drill or manual key, for applying angular force, and a cable 60 for transmitting torque from the driver to the roller, this cable being contained within a flexible accessing shaft 62 to which the device is attached. The roller has a cylindrical end cap 64 which is mounted on a post 66 on the frame for rotation thereon, through its connection to driving cable 60 that extends through the post.

With reference to FIG. 2B, roller 54 is scalloped along its length, providing three elongate tissue-capture chambers, such as chamber 70, which are distributed radially about the roller, and which successively engage and release tissue, as the roller is rotated. In the embodiment illustrated in FIGS. 2-7, the vacuum conduit serves to connect the external vacuum source to the roller, to provide a vacuum to each roller chamber successively as that chamber advances toward arm 56 in a tissue-acquisition operation. To this end, the vacuum conduit includes a sealed vacuum connection between the end face 71 of post 66 and the confronting face 73 of the roller (FIG. 2A), connecting an external vacuum source through a conduit 68 in post 66. As seen best in FIGS. 3A-3D, where the direction of rotation is indicated by arrow 72, the vacuum connection includes a bean-shaped recess 74 formed in face 71 of the post, and a vacuum port 76 at the end of conduit 68 in the post. The confronting face of the roller cap has three vacuum ports, one associated with each of the three chambers, such as port 76 associated with chamber 70. Each port is sealed by an O-ring (not shown) that rotates with the roller and which acts to seal the connection between that port and recess 74, as the port moves over the recess. As can be appreciated from FIGS. 3A-3D, rotation of the roller in a clockwise direction in the figures brings each chamber port and the associated chamber successively into vacuum communication with recess 74 on the frame post, producing a vacuum in chamber as the chamber approaches the bottom edge of arm 56 (about 6 clock in FIG. 3A), and which maintains the vacuum as the chamber rotates into a confronting relationship with the arm (about 9 o'clock in FIG. 3B). Continued roller rotation brings each adjacent chamber in an out communication with the vacuum source, as can be appreciated from FIGS. 3C and 3D.

FIGS. 4A-4C illustrate the operation of the device in acquiring a tissue fold, indicated at 80 in the figures. In FIG. 4A, the device has just been placed against a tissue region, where vacuum applied to roller chamber 70 acts to draw a nascent tissue fold 80 into the chamber. FIG. 4B shows the tissue fold being moved into tissue gap 58 as chamber 70 is rotated to about a 9 o'clock position. The figure also shows the next-in-line roller chamber (near a 4 o'clock position) moving toward a "vacuum" position at which that chamber will be connected to the vacuum and engage for an adjacent tissue. This process is repeated at each ⅓ turn of the roller, as shown in FIG. 4C, as each chamber is successively connected to the vacuum source, draws tissue into the chamber, moves the acquired tissue into the tissue gap, then releases the tissue as the vacuum connection to that chamber is broken.

In an alternative embodiment, not shown, the vacuum connection between the frame and successive roller chambers is effected by three chamber-associated recesses, e.g., bean-shaped recesses, formed in the roller cap face, for successively moving across a single vacuum port formed in the confronting face of frame post 66 as the roller is rotated, with a vacuum seal being provided by an O-ring covering the port in the frame post. In a related embodiment, each of the three recesses formed in the roller cap are replaced by a series of closely spaced individual ports that maintain a continuous vacuum connection between the frame port and each chamber, as the individual ports are moved across the fixed vacuum port in the frame.

Figure 5A:
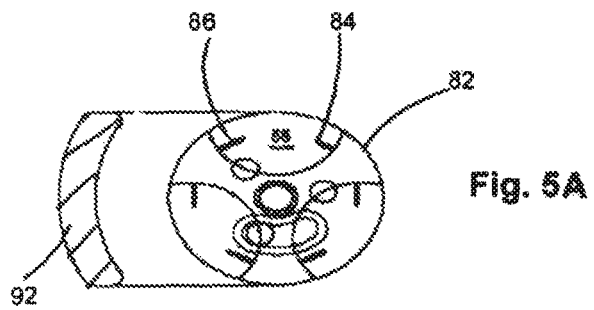
FIGS. 5A and 5B are sectional views like those in FIGS. 3A-3B, but showing different pin configurations for the roller and arm in the device.
Figure 5B:
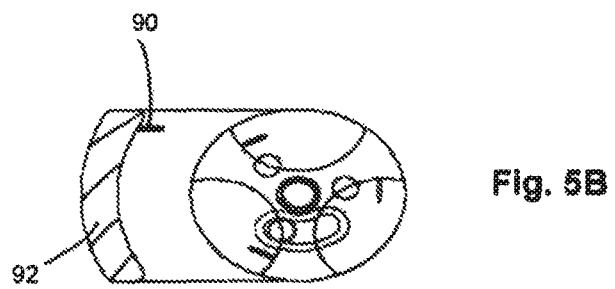
Figure 6A:
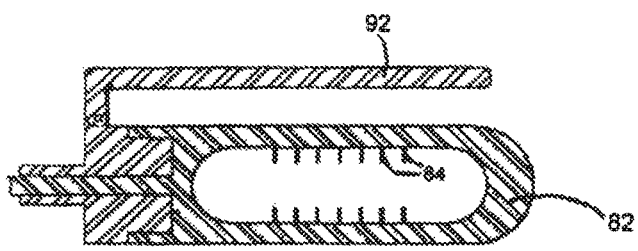
FIGS. 6A and 6C are side sectional views for the device shown in FIG. 2A, but showing how pins on the roller bend and slide for tissue engagement and release at different rotational positions of the roller, shown in FIGS. 6B and 6D, respectively.
Figure 6B:
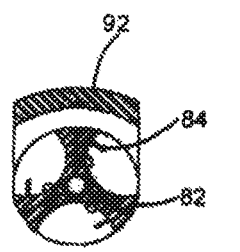
Figure 6C:
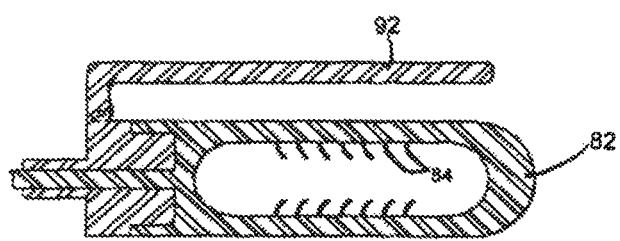
Figure 6D:
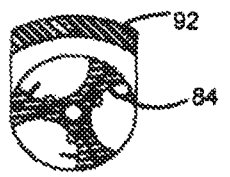

FIGS. 5A and 5B shows related embodiments of the device just described. In FIG. 5A, a roller 82 has rows of pins, such as pins 84, 86, extending in both directions in each roller chamber, such as chamber 88. The device in FIG. 5B includes a row of pins 90 near the upper, exit edge of arm 92. In both embodiment, the pins can be rigid, e.g., stiff metal pins, or flexible in the direction of roller movement, to minimize tissue tearing as each chamber releases its engaged tissue. This feature is further illustrated in FIGS. 6A-6D which shows pins 84 in a straight condition when tissue is first engaged (FIGS. 6A and 6B), and a bent condition when tissue is released from a chamber.

Figure 7A:
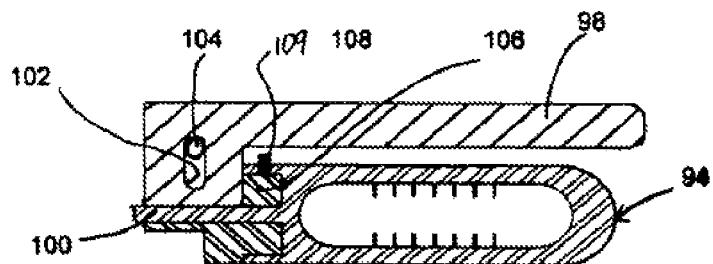
FIGS. 7A-7E show various mechanisms for mounting an arm on the device and for adjusting its position with respect to the roller.

FIGS. 7A-7E illustrate various embodiments of a roller-arm device like that described above, but showing different arm configurations and arm-positioning mechanisms used to move the arm between an open condition in which the arm and roller can embrace a side region of an already formed tissue fold, and a closed condition in which a tissue fold can be formed in the device by rotating the roller. In FIG. 7A, a device 94 has a roller 96 carried on a frame 100, and an arm 98 attached to a frame for movement toward and way from the roller. The arm-positioning mechanism, indicated at 106, is carried on frame 100 and is activatable, e.g., by a solenoid, pneumatic cylinder, or worm-screw mechanism, between extended and retracted conditions, to control the position of the arm through a piston 109. The positioning mechanism may be provided with internal spring biasing to allow limited movement of the arm toward and away from the roller at the arm's closed position, to accommodate variations in the thickness of the plication being drawn between the roller and arm. A pin 104 carried on the frame rides within a elongate slot 102 formed in the base of the arm, limiting vertical travel of the arm between the closed position shown, and an open, extended position.

Figure 7B:
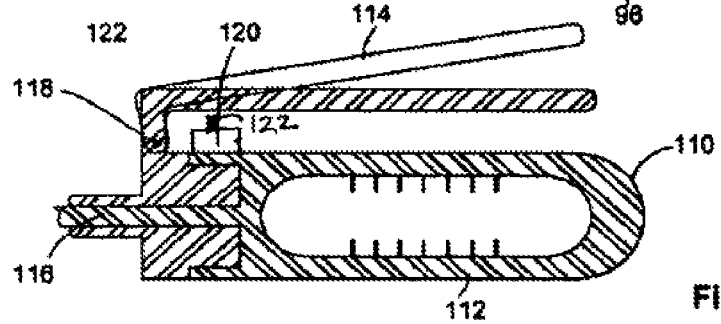

FIG. 7B shows a similar device 110 having a roller 112 and arm 114 mounted on a frame 116, but where the arm is pivotally mounted, at 118 on the frame for swinging movement between open (no shading) and closed (cross-hatch shading) positions, under the control of a solenoid 120 connected to the arm through a curved piston 122.

Figure 7C:
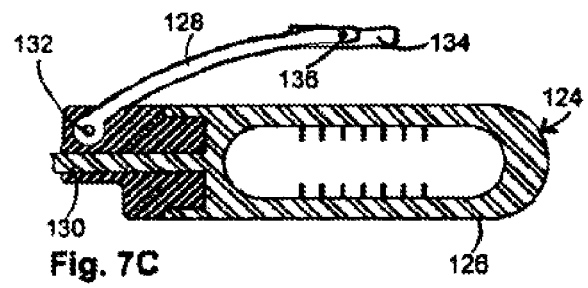
Figure 7D:
Figure 7E:
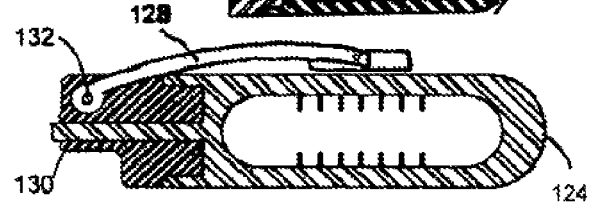

In roller/arm device 124 shown in FIGS. 7C-7E, arm 128 has are arcuate shape in side view, and is pivotally mounted on frame 130 at 132, for swinging movement between open (FIG. 7C) and closed (FIG. 7E) positions, under the control of an arm-positioning mechanism (not shown). A plate 134 pivotally mounted on the free end of the arm allows the arm to track the surface of the tissue fold during tissue acquisition; the ability of the plate to secure a tissue layer can be enhanced by tissue-engaging pins, such as shown at 136 in the embodiment of the device shown in FIG. 7D.

In another general embodiment, not shown, the roller has a plurality of tissue-engaging projections distributed radially about the roller, for engaging tissue as the roller is rotated in a tissue-advancing direction, but the vacuum is applied to the arm, such that tissue is drawn between the roller and arm by successive engagement of the roller with new tissue, while a layer of tissue fold opposite the roller is substantially immobilized by vacuum adherence to the arm. For example, the roller may include a stationary, slotted face structure having a outer surface facing the arm, where tissue engagement is effected by pins that rotate under the influence of the roller driver, extending through slots in the face plate on the entrance side of the arm, and retracting away from the face plate on the exit side of the arm.

Figure 8A:
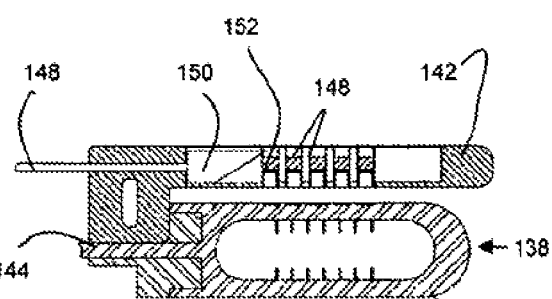
FIGS. 8A and 8B show a staple-holder and drive mechanism in the arm of a tissue-acquisition device, where staple driving is done either by a pushing or pulling action, respectively.
Figure 8B:
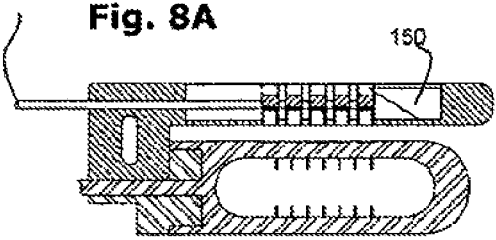

The tissue-acquisition device of the invention may include an independently movable and operable fastening mechanism, or may incorporate a fastening capability into the arm and roller structure of the device. FIGS. 8A and 8B illustrate a tissue acquisition device 138 having a roller 140 and an arm 142 mounted on a frame, as described above. Although not shown here, the device may include an arm-positioning mechanism for moving the arm toward and away from the roller. Arm 142 is provided with a plurality of staple-holding slots, such as slots 146, each for holding a one or more U-shaped staples (not shown) therein. The staples are ejected from the arm by remotely pushing a rod 148 in a proximal-to-distal direction, causing an angled pusher blade 150 to engage in a staple plate 152, pushing the plate downwardly in the figure and ejecting a staple toward the roller. In a tissue-fastening operation, the arm is moved by the arm-positioning mechanism to a fastening position close to the roller, to form a tissue gap of preferably between 60-120 mils, and locked in place. Activation of the pusher blade then ejects the first-encountered staple through the compressed tissue fold and against the roller, which is positioned to present an anvil surface to the arm, for fastening the staple through the tissue. The device shown allows five such staple operations, so that an extended tissue fold made up of up to five individually fastened tissue folds can be formed with consecutive tissue-acquisition and fastening steps.

The embodiment shown in FIG. 8B is similarly constructed, except that the staple ejection blade, indicated at 150', is operated in a distal-to-proximal direction, by applying a pulling force to a pull rod 148' connected to the blade.

Figure 9A:
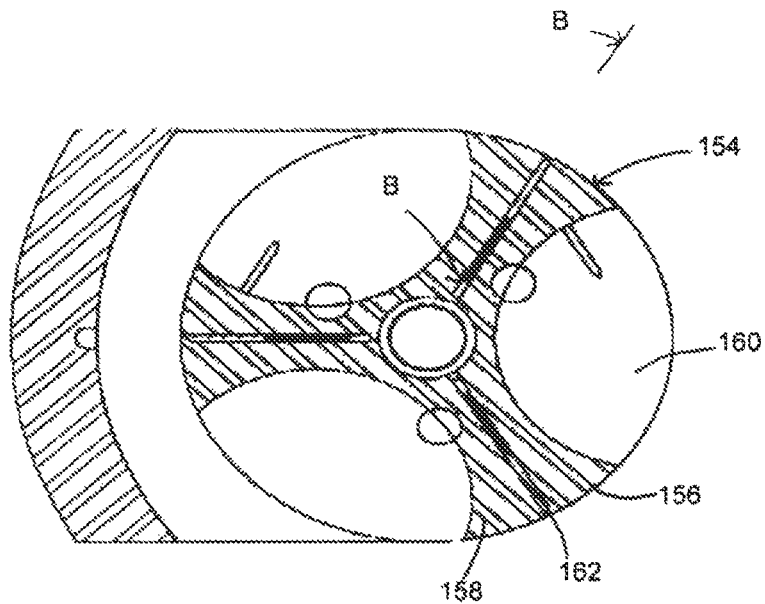
FIGS. 9A and 9B shows a cross-sectional view through a tissue-acquisition device in which the staple holder and staple-drive mechanism are contained in the roller of the device (FIG. 9A), and a cross-sectional view, through line B-B in FIG. 9A showing staple firing from the roller (FIG. 9B)
Figure 9B:
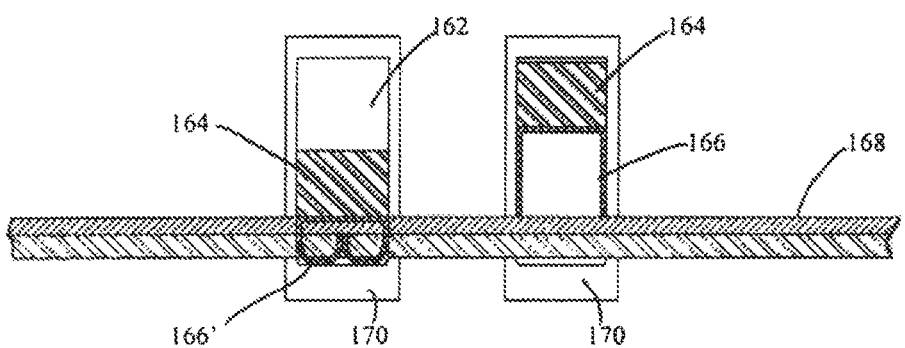

FIGS. 9A and 9B illustrate an embodiment of a tissue-acquisition device 154 in which staples are held in and ejected from the device roller, indicated at 156. As seen in FIG. 9A, roller 156 is formed of three laterally extending columns, such as column 158, adjacent pairs of which define the three tissue chambers, such as chamber 160, in the roller. Formed in each column is a plurality of staple-holding slots, such as slot 162 in column 156, where the slots in each column may be arranged side-by-side in a laterally extending direction (perpendicular to the plane of the page), similar to the staple holding configuration shown in FIGS. 8A and 8B, but preferably near the free end of the roller only. Thus, for example, a roller having two laterally arranged staple slots in each column will contain a total of six staples that can be used for tissue fastening during an operation. FIG. 9B shows two laterally arranged slots 162 in a roller column, from the perspective of the B-B view line in FIG. 9A. As seen, each slot provides a staple plate 164 which, when moved from a raised to a lowered position in the figure, e.g., by a staple-ejection mechanism like that shown in FIG. 8A or 8B, pushes a staple 166 from its slot, through a compressed tissue plication 168 and against the device's arm 170, which serves as the anvil in a stapling operation. In operation, once a suitable amount of tissue fold has been formed in the device, the device arm is moved to a position close to the roller, preferably within 60-120 mils of the roller and locked into place. The staple ejection mechanism is then activated to eject one or more staples through the compressed tissue fold, against an anvil surface of the arm, to fasten that fold.

In another embodiment, the fastening mechanism incorporated into the tissue-acquisition device employs one or more U-shaped fasteners, each having a pair of elongate, side-by-side legs that are preformed to adopt the shape of loops when the fastener is ejected from a staple slot. Typically, a plurality of such fasteners are held in an end-to-end configuration in a slot formed in the device arm and extending from the proximal end of the arm to a distal tip, where the fasteners are ejected against a tissue fold. In this embodiment, the roller-confronting arm is provided with a channel through which the clips are advanced, and the roller serves as the anvil. The roller-arm device can be similarly adapted for use with the linear stapler described in Section H, the coil-wire fastener described in Section J, and the barbed anchor fastener described in Section K.

D. Auger-Blade Tissue-Acquisition Device and Method

Figure 11A:
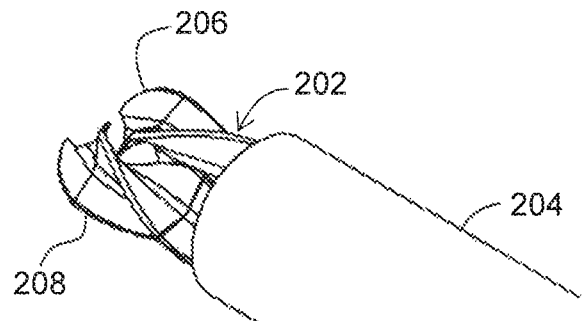
FIGS. 11A-11C illustrate an auger-blade tissue-acquisition device constructed in accordance with yet another aspect of the invention, shown in initial deployment (FIG. 11A), full-blade deployment (FIG. 11B), and tissue-engaging condition (FIG. 11C).
Figure 11B:
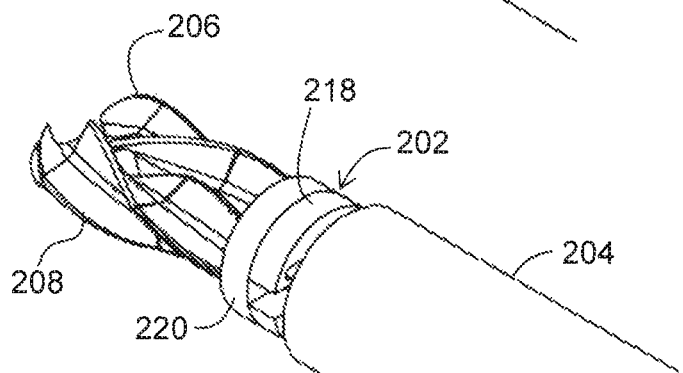
Figure 11C:
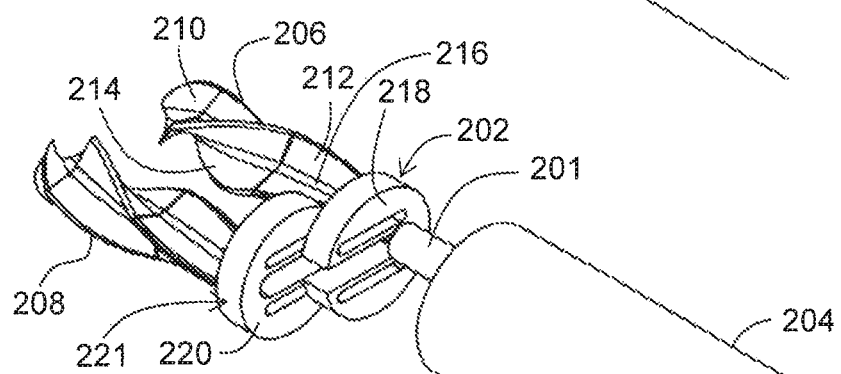

Another tissue-acquisition device constructed in accordance with the invention is the auger-blade device 202 seen in FIGS. 11A-11C. Shown here is the distal end of a flexible shaft 204 used to access a hollow organ, e.g., the stomach, and to manipulate the position of the device within the organ. It will be understood that shaft 204 houses control elements, e.g., cable and/or pneumatic tubes, for controlling the operation of the device remotely at the proximal shaft end.

Figure 12:
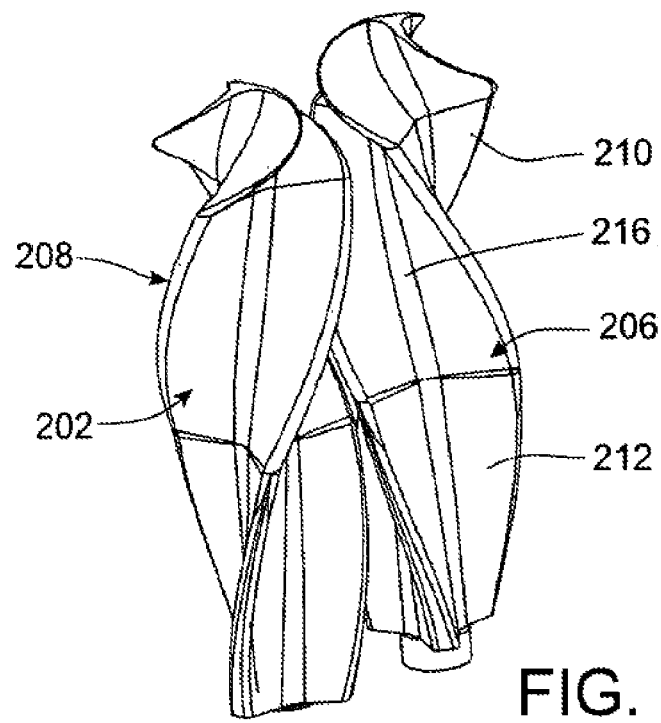
FIG. 12 shows, in enlarged view, the shape of the helical blades in the auger-blade device.

As seen in the figures, device 202 includes a pair of auger blades 206, 208, each having three helical fins, such as fins 210, 212, 214, in blade 206 extending from central stem 216. As seen best in FIG. 12, which shows the blades in enlarged view, each blade fin has a relatively high helical pitch at its upper, distal end, a relatively low helical pitch at its lower-proximal end, and an intermediate helical pitch between the two blade ends. The high helical pitch at the blades' distal ends has been found most effective for engaging tissue, when the blades are placed against tissue under operational conditions, described below. The intermediate pitch between the two blade ends is effective in maintaining a tissue grasp during operation, and the low pitch near the bottom of the blades acts to avoid bunching of the tissue fold formed during operation. As can be appreciated from FIGS. 11A and 11B, the two blades are partially interleaved to reduce the total blade-to-blade width profile of the device to only slightly greater than ⅜ inch, for limiting the diameter of shaft 204, which is used in carrying the device into the stomach, to no more than about half an inch.

With continued reference to FIGS. 11A-11C, blades 206, 208 are rotatably mounted on circular bases 218, 220, respectively. The two bases, which form a frame 221 in the device, are slidably mounted together for movement toward and away from one another, and are biased toward the stacked, low profile condition seen in FIGS. 11A and 11B by a coiled spring (not shown). When tissue is acquired during operation of the device, the captured tissue forces the blades apart, to an offset condition such as seen in FIG. 12C, with the spring biasing force acting to keep the blades pressed firmly against the captured tissue.

Blade 206 in the device is connected to a rotational drive 201 provided in shaft 204 for rotating that blade during operation. Although the opposite blade may also be under the control of a rotating drive source, it is preferably free to rotate in response to forces applied on it by the driven blade during tissue acquisition. As can be appreciated, the two blades will counter-rotate as tissue is fed by the driven blade between into the gap between the two blades.

Figure 13:
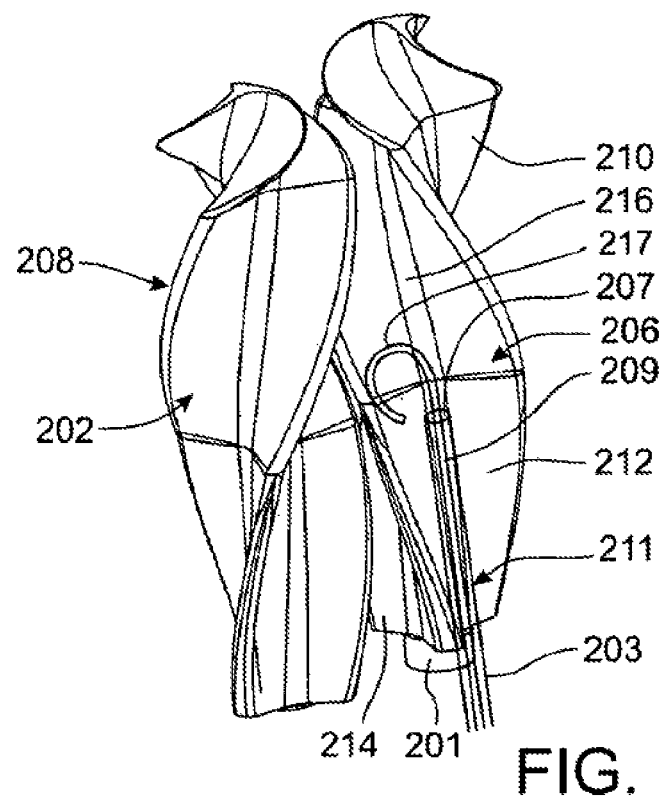
FIG. 13 illustrates elements of a wire loop fastener mechanism in the device.

FIG. 13 shows elements of a fastener mechanism 211 in the device. A wire-feed conduit 203 in this mechanism extends through drive 201, base 218 (FIG. 11C) and stem 216 in blade 206 and terminates at an opening 207 formed in the stem. The conduit carries a plurality of pre-formed wire coil segments, such as segments 209, which can be ejected, individually through opening 207 during operation of the device. The wire segments are preformed to assume closed elliptical loops, such as loop 217, when they are ejected from the conduit. The wire loop is dimensioned to encircle two layers of a plication formed between the auger blades, to fasten the captured tissue fold.

In operation, the device is introduced into an internal organ, e.g., a stomach, with the blades and fastener fully retracted within shaft 204. Once in the stomach, the device is extended from the shaft and placed against the tissue to be acquired, typically by placing the blades at an angle with respect to the tissue, such that the blades contact the tissue both at their distal ends and distal-end side regions. The blade drive mechanism is now engaged to drive blade 206, resulting in tissue take-up between the two blades, with the biasing force between the two blades accommodating the additional bulk between the blades, and serving to keep the plication being formed in a relatively compressed condition. When a suitable amount of tissue fold has been taken up, a pusher in the shaft is activated to expel a pre-formed wire segment from opening 207, to fasten that tissue fold. The blades are driven in the reverse direction to "unwind" and release the fastened tissue. The procedure may be repeated for successive folds, e.g., adjacent folds that will form a continuous two-layer fold in the stomach.

E. Scissor-Arm Cage Device and Method

Figure 14B:
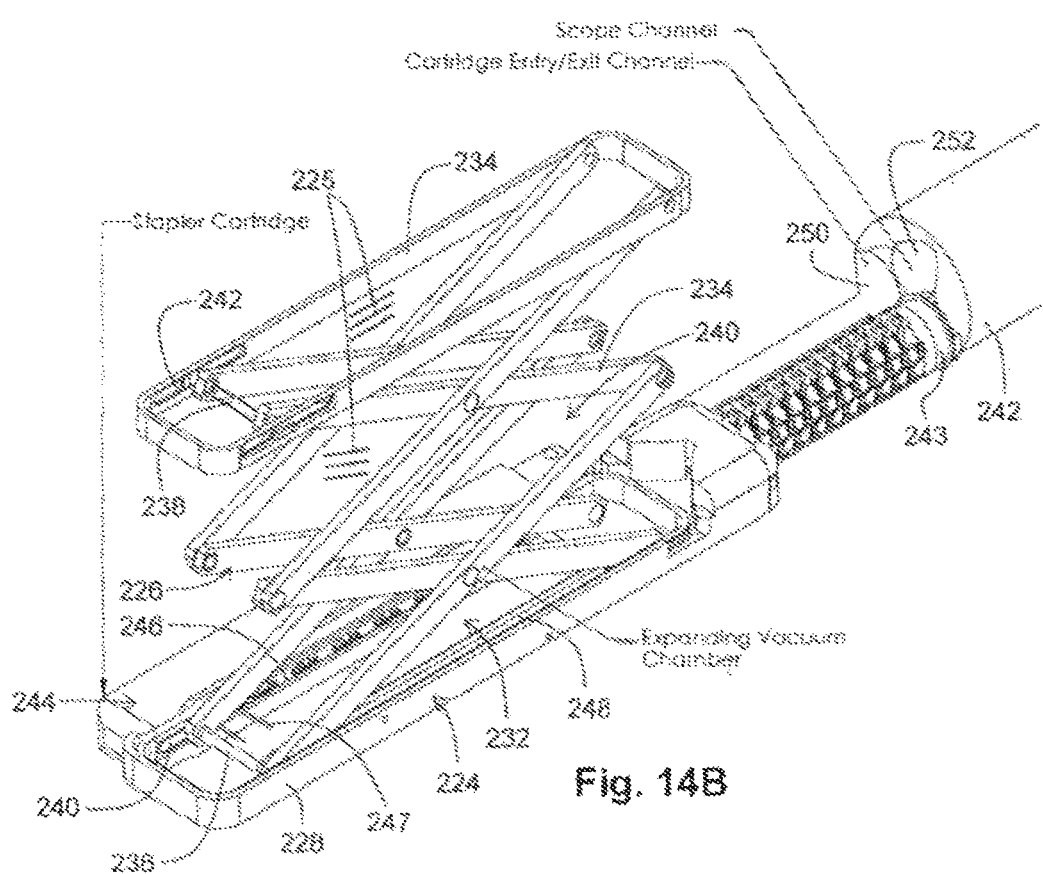

FIGS. 14A and 14B B show in perspective view, a scissor-arm cage device 224 for use in forming a tissue fold, in accordance with another aspect of the invention. The device is carried art the distal end of an intraoral-access shaft 242 through which a drive mechanism and vacuum tube are supplied to the device through a flexible shaft connector 243. The shaft, which forms part of the device, also provides a channel 252 for an endoscope and a channel 250 through which staple cartridges can be removed and resupplied to the device during operation, as described below.

The device has a rigid frame 226 formed by a lower and upper rectangular frame members 228 and 230, respectively, where the lower frame member defines an opening 232 for tissue acquisition. The two frame members are joined by a scissor-arm structure 234 in the frame which is expandable from collapsed-arm condition, shown in FIG. 14A, which provides a low profile for intraorally accessing the stomach, and the expanded-arm condition shown in FIG. 14B, for tissue acquisition within the stomach. As can be appreciated, the scissor-arm structure is movable between its collapsed and expanded positions by movement of slider pins 236, 238 which move within slots 240, 242 formed in the upper and lower frame members, respectively. The lower pin is connected to a worm drive 243, which can be activated remotely, once the device is in the stomach, to place the device in its tissue-acquisition position, and to place the device in its low-profile condition for removal from the stomach.

Frame 226 is covered by a flexible membrane, indicated by lines at 225, formed over the structure 234 and the upper end of the frame, but not opening 232 at the lower end of the frame. With the cage in its expanded condition, the membrane forms a columnar tissue-chamber 240 having a lower tissue-acquisition opening 232 and a rectangular cross-section. Vacuum is supplied to the chamber, during a tissue-acquisition operation, by a vacuum port in the chamber (not shown) connected to an external vacuum source. Where the device is designed for intraoral use, it is carried at the distal end of a flexible shaft for intraoral access, such as indicated at 242.

Device 224 also further includes a fastening mechanism, such as the linear stapler shown at 224, and described in detailed in Section G below. Briefly, the fastener includes a staple cartridge 246 which holds a linear array of staples and which can be operated remotely to simultaneously eject the array of staples, such as staple 247 shown in the figure, and an anvil 248 which is moveable between an retracted position which allows tissue acquisition into the opening of the device, and a fastening position in which the anvil is moved toward the staple holder to (i) squeeze a tissue fold capture in the tissue chamber and (ii) provide an anvil surface against which the ejected staples are crimped over the tissue fold, to fasten the same. The anvil is pivotally mounted on a pair of arms (not shown) which can be operated to pivot outwardly, across the cage opening, to place the anvil in its fastening position adjacent the stapler housing. Once the staples are fired, and the captured tissue is fastened, the cartridge can be removed and replaced through a channel 250 in shaft 242, with the shaft retained in place in the patient's throat, esophagus and stomach. As seen in FIG. 14B, the shaft also includes a channel for an endoscope. Alternatively, the fastener in device 224 device may incorporate a multi-fire fastener, such as the one of the fasteners described below in Sections H, I, and J.

In operation, the device is placed in its collapsed arm condition for intraoral placement, and its open end then placed against a selected tissue region, e.g., along a preselected fold line in the stomach. Screw-drive 243 is remotely activated to expand the chamber, and vacuum is supplied to the chamber to draw a tissue fold into the chamber. The fastener is then actuated to (i) move the anvil into a position that squeezes the tissue fold between the anvil and staple head, and (ii) eject one or more staples through the base of the squeezed tissue fold.

If it is desired to capture an adjacent tissue fold, in practicing the method for stomach volume reduction described in Section A, the cage is removed from the first fold, by release of chamber vacuum, and placed so that its opening straddles a side portion of the just-formed fold and a "basement" region of the adjacent tissue. When vacuum is again applied in the chamber, a fold of tissue that is continuous with the just-made fold, but which extends the fold in a downstream direction, is created. This process may be repeated until a desired-length of continuous two-layer fold is formed.

F. Hollow Tube Tissue-Acquisition Device and Method

Figures 15A, 15B:
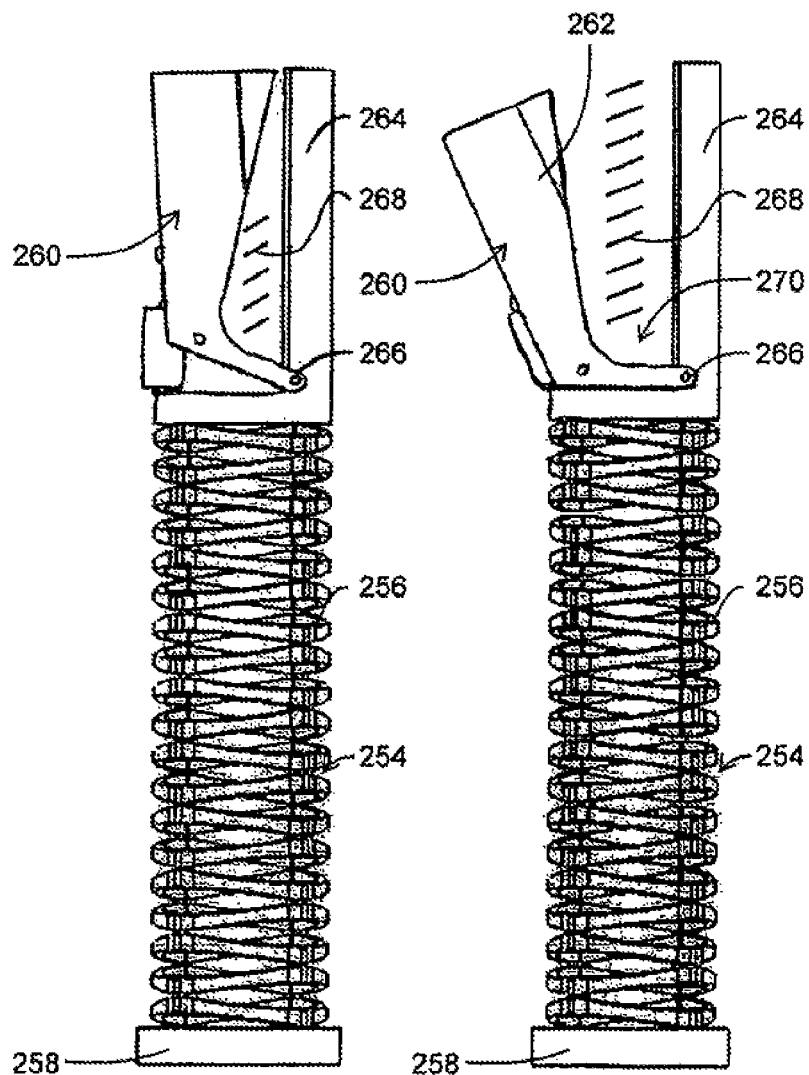
FIGS. 15A and 15B illustrate a hollow-tube tissue-acquisition device acquisition device formed in still another aspect of the invention, shown in closed (FIG. 15A) and open (FIG. 15B) condition.

In another aspect, the invention includes a hollow-tube tissue-acquisition device 254 for acquiring and fastening a tissue fold. As seen in FIGS. 15A and 15B, device 254 has an elongate, flexible hollow tube 256 into which tissue can be drawn with application of a vacuum to the tube, via a vacuum tube supplied through a shaft, whose connection to tube 256 is shown at 258. The shaft is designed and dimensioned for introducing the device intraorally into a patient's stomach, and includes proximal-end controls by which a user can control the operation of the device outside the patient's body after intraoral placement of the device within the patient's gastrointestinal tract. The shaft also accommodates an endoscope (not shown) used for viewing within the stomach.

A stapler head 260 carried at the distal end of the tube includes a stapler assembly 262 and an anvil frame 264. The stapler assembly is pivotally mounted at 266 on an anvil frame 264 for pivoting movement between an open position (FIG. 15B) in which tissue can be drawn into the tube, and a closed, stapling condition (FIGS. 15A and 16A-16C). The stapler assembly position is controlled by a cable or the like (not shown) which can be operated remotely to move the assembly between its open and closed conditions. The sides of the fastener are covered by a flexible membrane 268 which forms with the stapler assembly and anvil frame, a distal-end chamber 270 through which tissue can be drawn into tube 254, when a vacuum is applied to the tube, through a vacuum tube carried in the shaft of the device.

As seen best in FIGS. 16A-16C, anvil frame 264 provides a vertically extending arm 272 which terminates near its distal end in a curved anvil surface 273. Stapler assembly 262 has a staple holder 275 for holding a stack 277 of staples at a fixed position in the assembly. The drive mechanism for ejecting staples from the assembly includes front and back assembly plates 276, 274, respectively, and a wedge member 278 disposed between the plates, and attached to a cable (not shown) which is pulled to activate staple driving. The front plate, which is pivotally mounted in the assembly at 280, carries at its distal end, a staple driver 282 for engaging and ejecting the top-most staple, such as staple 277a, in the staple stack. As can be appreciated from the series of moved positions in FIGS. 16A-16C, pulling wedge member 278 in a proximal direction, i.e., top-to-bottom direction in the figures, causes plate 274 to pivot toward the anvil, which in turn causes the staple driver to engage and eject the topmost staple in the stack, forcing it through a tissue fold captured at the end of the fastener and crimping it against the anvil.

In operation, for use in acquiring a tissue fold in a body tissue or organ, the device is introduced into the patient's stomach or other internal organ, with the fastener in its closed, low-profile condition. Once opened, the distal end chamber formed by the stapler head is positioned against the body tissue or organ, and a vacuum is applied to draw tissue through the distal-end chamber into tube 256, forming a tissue fold within the tube. The stapler assembly is then moved to its closed condition to clamp the tissue fold at its base, and then activated to eject a staple across the squeezed tissue fold. Once the fold is fastened, the staple holder is opened, allowing the tube to be withdrawn and either removed from the patient's stomach or placed at another position for additional tissue acquisition and stapling. In particular, for use in forming a series of in-line folds within the stomach, the steps above are repeated along a preselected tissue-fold line within the stomach.

G. Linear Stapler Device

Figure 17:
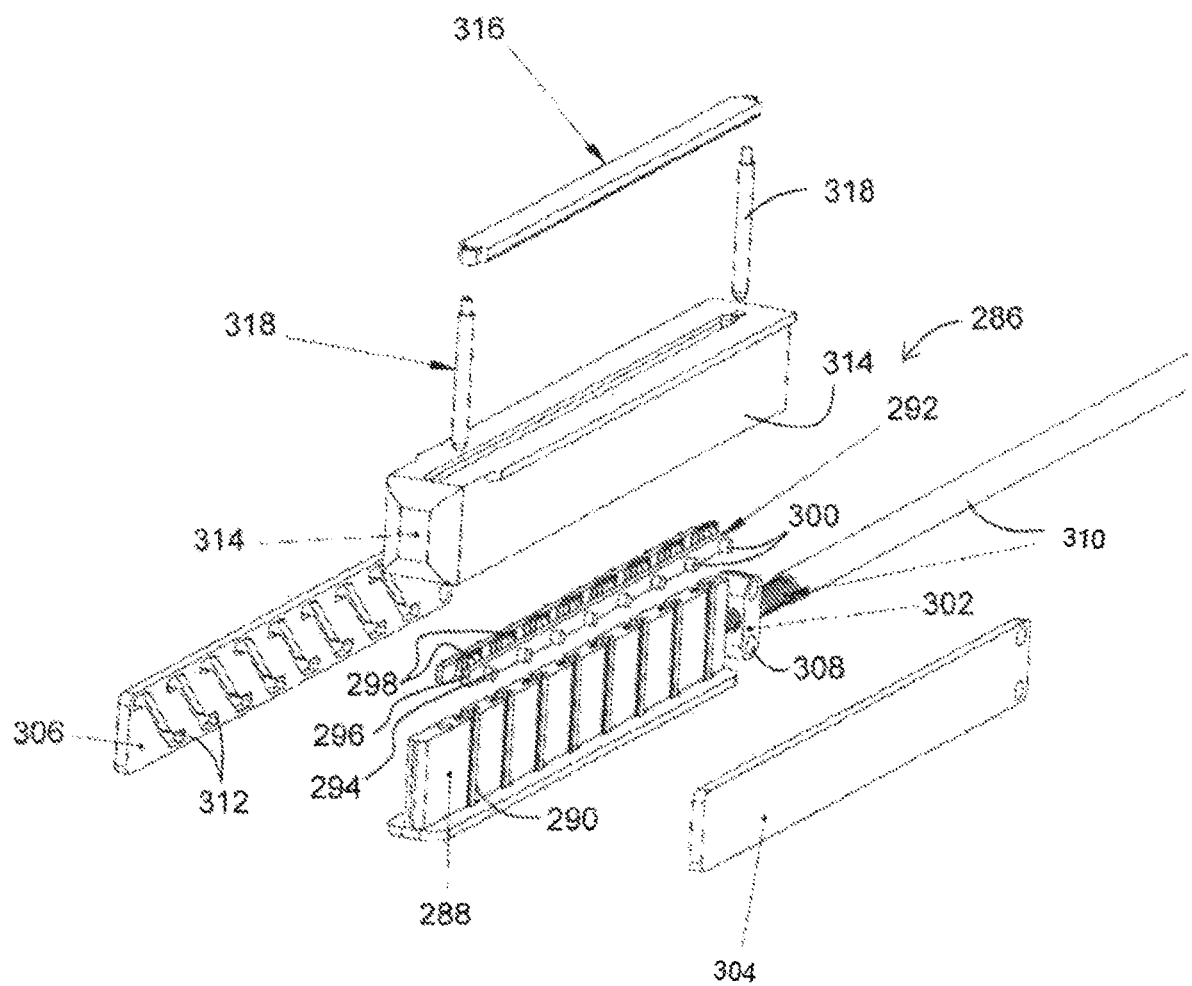
FIG. 17 shows, in exploded view, a linear stapler device formed in accordance with an aspect of the invention.

FIG. 17 shows, in exploded view, a linear stapler device 286 constructed in accordance with an aspect of the invention, and designed to fasten tissue, such as a two-layer tissue fold, with a linear array of simultaneously applied staples.

The device includes a staple cartridge 288 having a plurality of U-shaped slots for holding a linear array of staples, such as slot 290 holding a U-shaped staple 291, seen in FIGS. 18B and 18C. A pusher assembly 292 in the device is formed of a pair of side bars 294, 296 that support between them a plurality of pusher elements, such as elements 298, that are positioned to engage the lower surfaces of the staples held in the associated slots in the cartridge. Each side bar in the pusher assembly is provided with a row of pins, such as pins 300, for a purpose to be described.

An ejector assembly 302 in the device includes a pair of pusher plates 304, 306 that are each fastened at their right end regions in the figures to an end connector 308 (FIGS. 18A-18C) that is turn is attached to a drive mechanism 310, such as a worm drive. The interior-facing sides of the plates are provided with a plurality of slots, such as slots 312 seen in plate 306 in FIG. 17 and slots 313 seen in plate 304 in FIGS. 18A-18C, and having the angled configuration seen in FIG. 17. In its assembled state, the pins on opposite sides of the ejector assembly are carried in associated slots in plates 304, 306, and the entire device is encased in a housing 314 that holds the staple cartridge in a stationary position and allows the ejector assembly to be moved in a distal direction (left-to-right in the figures) relative to the staple cartridge toward a retracted position.

Completing the description of the device, an anvil 316 is supported above the staple housing on a pair of supports 318 that are movable, by means of a suitable mechanism in the device, toward and away from a position in which the anvil can function to (i) squeeze a tissue fold captured between the anvil and staple housing, and (ii) provide crimping surfaces for crimping staples that are ejected from the staple cartridge, through a tissue fold, against the anvil.

The operation of the device in ejecting a linear array of staples is illustrated in the sequence of FIGS. 18A-18C. In 18A, the ejector assembly is in an initial load position in which pins 300 in the pusher assembly are carried in the lower ends of slots 312 in the two plates of the ejector assembly. As the ejector assembly is pulled to the right in FIG. 18B, the pins in the pusher assembly are forced upwardly within the angled slots in the moving plates, forcing the staples upwardly within the staple cartridge. In FIG. 18C, the staples are shown completed ejected from the cartridge as the ejector assembly is pulled to a fully retracted position in which pins 300 have been forced into the upper ends of the associated slots.

According to the invention, the linear stapling device assembly is readily adapted for integration into each of the four tissue-acquisition devices described in Sections C-F above. For example, the fastener holder described with respect to each acquisition device may be modified to provide the above-described cartridge and ejector assembly within housing 314, and the anvil described with respect to each acquisition device can be modified to provide the anvil in the current device. Alternatively, the linear stapler may be used as an independently operated stapling device.

H. Clip Fastener Device

FIGS. 19-21 illustrate aspects of the fastener and fastening device that may be used in a surgical procedure to fastening two tissue layers 322, 324. The delivery device includes an elongate arm 326 having an internal channel or slot 328 which accommodates one or more U-shaped fasteners, such as fastener 330 seen in FIG. 21D. The slot preferably has a trapezoidal cross-sectional shape and a length dimensioned to accommodate a plurality of fasteners arranged inline, as seen in FIG. 20.

Fastener 330 has a pair of elongate, side-by-side legs 332, 334 attached to a base portion 336 (FIG. 21D). The legs are preformed to adopt the shape of loops, as shown in FIG. 21C, when the fastener is ejected from arm 326. In one embodiment, for use in the tissue-acquisition and fastening method above, the fastener may be formed by laser cutting a titanium-ally tube, such as a nitinol tube, having the wall thickness of between 5 and 20 mills, and an inner diameter between 60-120 mils. The cut, tube-like structure is then forced into the fastener-arm slot, where it is constrained in a straightened condition, as in FIG. 20. When the fastener is later ejected from the arm, by the action of a pusher acting against the left end of the fasteners in FIG. 20, the fastener will return to its original shape, where the loops in the fastener, seen in FIG. 21C, will have approximately the original diameter of the tube from which the fastener was cut. In the specific embodiment references above, the loops will return to a diameter of between 60-120 mils, suitable for fastening a compressed stomach tissue fold.

FIGS. 21A and 21B illustrate other embodiments of the fastener of the invention. Fastener 338 in FIG. 21A has the same design, but substantially shorter legs, and thus smaller fastener loops. Fastener 190 in FIG. 21B has a single leg that returns to a single fastening loop after deployment.

FIGS. 19A-19C illustrate various fastener orientations in fastening a two-layer tissue fold. In FIG. 19A, fastener arm 326 is oriented at right angles to the tissue fold, but not pressed firmly against the fold. As seen, the expelled clip may not fully engage both tissue layers in this configuration. This problem can be overcome by pressing the tip of the arm more firmly against the tissue fold, compressing it to the thickness of a single tissue layer, as shown in FIG. 19B. Alternatively, the clip can engage both layers when arm 326 is place at a fairly steep angle with respect to the tissue, as seen in FIG. 19C.

Figure 22A:
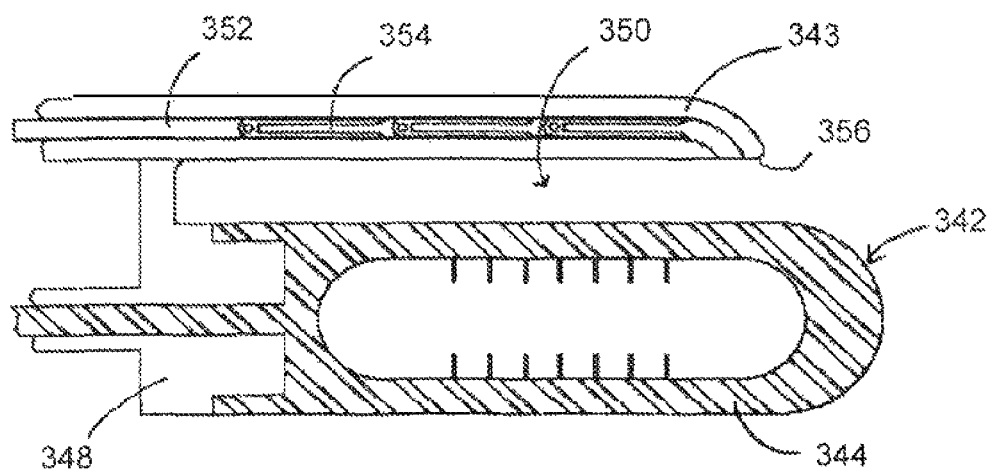
FIGS. 22A and 22B are side sectional views of tissue-acquisition devices having different arm-end geometries for releasing fasteners from an arm in the device against a device roller, shown in tissue-capture (22A) and tissue-fastening conditions (FIG. 22B)
Figure 22B:
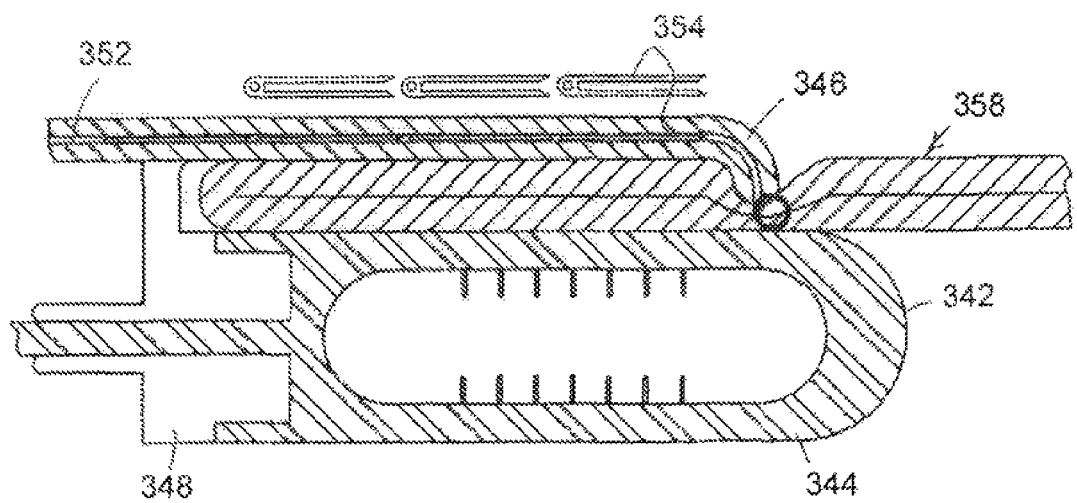

FIG. 22A shows an embodiment of a tissue-acquisition device 342 of the type described above having a roller 344 and arm 346 carried on a frame 348, for capturing a tissue fold in a tissue gap 350 between the roller and arm. As seen, arm 346 is provided with an internal slot 352 for holding a plurality of fasteners 354 in an end-to-end fashion, and is curved toward the roller at its open, distal end 356, for ejecting fasteners into a tissue fold captured between the roller and arm end, by activation of a pusher (not shown) in the arm.

In operation, device 342 is initially placed along one end of a fold line, and with the arm moved to a closed condition, the roller is operated to capture a tissue fold within tissue gap 350. When a desired amount of tissue has been captured, the arm is moved to a fastening position at which the tissue fold is squeezed between the roller and arm end, and the pusher is activated to eject a single fastener at an angle to the tissue fold, which fastens the tissue fold by self-forming loops, as illustrated in FIG. 19C. The arm of the device is then moved to its expanded, open condition, and the device is moved to an adjacent region at which a distal end portion of the device embraces a side of the just-formed fold. The arm is now moved again to its closed condition, and the tissue acquisition and fastening process is repeated to extend the original fold. By providing the device with N fasteners in the arm, a continuous elongate fold formed of a total of N individual folds can be produced.

FIG. 19B shows the same device 342, but where the distal end of arm 346' is bent to engage a tissue fold, shown at 358 in the figure, at a substantially right angle. The distal-end configuration is designed to press firmly into the fold, as in FIG. 19B, to ensure that the released clip forms engages both layers of the tissue fold.

According to the invention, the clip fastener device is readily adapted for integration into each of the four tissue-acquisition devices described in Sections C-F above. For example, the fastener holder described with respect to each acquisition device may be modified to provide a slotted arm carrying the pre-formed clips, and the anvil described with respect to each acquisition device can be modified to form a surface for supporting a tissue fold during clip ejection. Alternatively, the clip fastener may be used as an independently operated stapling device.

I. Coil-Wire Fastener Device

A third tissue-fastener device 360 constructed in accordance with the invention is shown in side view in FIGS. 23A-23D, where the four figures illustrate four operational stages of the device. Briefly, the device has a wire-feed plate 362 and an anvil plate 364 which are movable toward and away from one another between an open condition shown in FIG. 23A, which also shows a tissue fold 366 positioned between the plates, and a closed, clamping condition shown in FIGS. 23B-23C, which shows the same tissue fold being squeezed for fastening (FIG. 23B), and with a coil-wire fastener 368 partially formed in the fold (FIG. 23C). FIG. 23D shows the device moved back to its open condition after fastening the tissue fold with the completed coil-wire fastener. The two plates, which are seen in side view in the figures, are moved between open and closed positions by a remotely driven worm drive (not shown), although any suitable drive mechanism for raising and lowering the anvil plate relative to the wire-feed plate may be employed.

With continued reference to the figures, wire-feed plate 362 provides a straight wire channel 370 through which a wire 372 is fed to the plate in a right-to-left direction in the figures from a downstream wire-delivery tube 374. A deflection member 376 at the open end of the channel 370 functions to deflect the fed wire in an upward direction in the figures as the wire is advanced into and through the tissue fold, as seen in FIG. 23C. In addition, anvil plate 364 provides a semi-circular track 378 that further bends the wire toward a circular coil as the wire is advanced through and over the top of the tissue fold, and back through the fold in the opposite direction.

FIGS. 24A-24E illustrate various wire configurations that are contemplated for the device, where the direction of wire feed is in a right-to-left direction in the figures, consistent with FIG. 23, as indicated by arrows 381. FIGS. 24A and 24B show a continuous wire 380 having a plurality of coil-wire segments, such as segments 382, 384, separated by breakaway segments, such as segment 386 (FIG. 24B), composed of a tapered section 388 at the upstream end of segment 384, and a small-diameter link 390 joining the tapered section to the base of the downstream end of segment 382, as seen in FIG. 24B. Wire 380 is designed to break at the downstream end of each coil-wire segment, as the downstream end of the segment encounters and is bent by the deflection member in the device. That is, the small-diameter link is sufficiently thin that the bending force it encounters at the deflection member is sufficient to snap it and release the next-in-line segment. This both allows the wire to form a series of identical-length coil-wire fasteners, without having to separately shear the wire, and also provides a tapered upstream end on each new wire segment, to facilitate entry of the segment into a tissue fold.

FIGS. 24C and 24D show a discontinuous wire 392 having a plurality of nested wire segments, such as segments 394, 396, which are joined end-to-end by nesting a pointed tip 398 at the upstream end of one segment, such as segment 394, in the downstream end channel in an adjacent segment, such as downstream channel 400 in segment 396. As can be appreciated, the nesting arrangement allows the coil wire segments to form desired-size coil fasteners without cutting, and provides a pointed tip for facilitating entry of each wire into a tissue fold.

FIGS. 24E and 24F show a discontinuous wire 402 having a plurality of blunt-end wire segments, such as segments 404 and 406, which abut one another as the wire is being advanced through a feed tube. The configuration allows the coil wire segments to form desired-size coil fasteners without cutting.

In operation, the device is positioned with its wire-feed and anvil plates positioned about a tissue fold to be fastened, as shown in FIG. 23A, and the plates are brought together to squeeze the fold prior to fastening, as shown in FIG. 23B. The wire in the feed tube is then advanced in a right-to-left direction in the figures, causing the next-in-line wire segment to deflect toward the fold, penetrate the fold, then curve backwards on itself in forming a coil-wire loop fastener, as shown in FIG. 23C. In the embodiment shown in FIGS. 24A and 24B, the deflection force snaps the wire at the downstream end of a coil-wire segment, releasing the coiled segment from the next-in-line segment in the feed tube. In the other embodiments shown, each wire segment is simply released when coiled-wire formation is complete. Once the tissue is fastened, the feed and anvil plates are opened to release the fold and move to a next fold or fold region to be fastened, in a multi-fire operation.

According to the invention, the coil wire fastener device is readily adapted for integration into each of the four tissue-acquisition devices described in Sections C-F above. For example, the fastener holder described with respect to each acquisition device may be modified to provide a feed tube by which the fastening wire can be advanced toward a deflection member in the fastener holder, and the anvil described with respect to each acquisition device can be modified to provide a curved, e.g., semi-circular track by which advanced wire is further bent toward a circular wire fastener.

J. Barbed-Anchor Fastener

Another tissue-fastening device constructed in accordance with the invention is shown at 408 in FIGS. 25A-25E. The device is carried partially within and also extends from the distal end of a flexible shaft 410, by which the device can be introduced into a hollow organ, e.g., a patient's stomach, and which provides, at its proximal end, user controls for controlling the operation of the device, as will be appreciated from the description of the device below. The shaft may include an endoscope, not shown, for use in visualizing the placement of fastener anchors at tissue-fold sites.

Figure 25A:
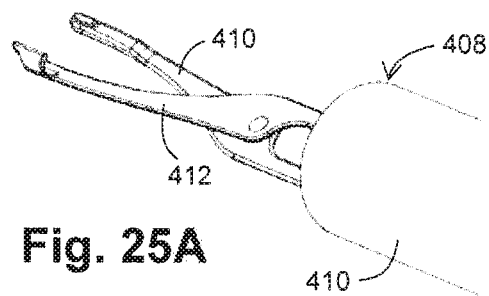
FIGS. 25A-25E illustrate construction and operation of a barbed-anchor fastener device constructed according to another embodiment of the invention.
Figure 25B:
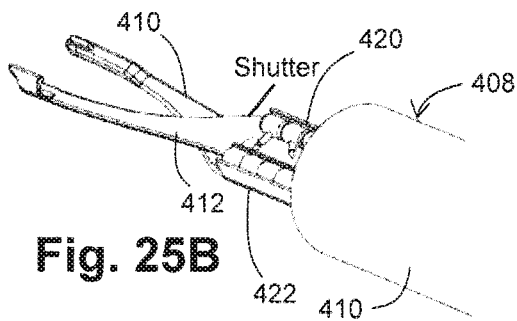
Figure 25C:
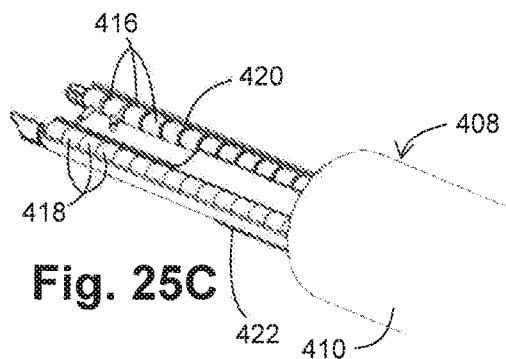
Figure 25D:
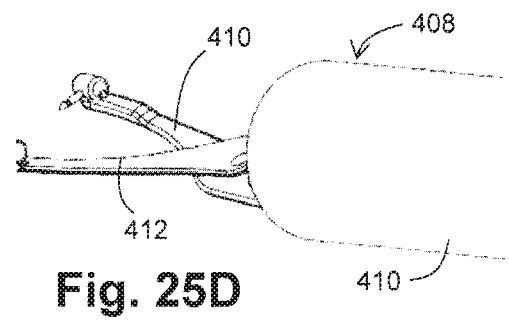
Figure 25E:
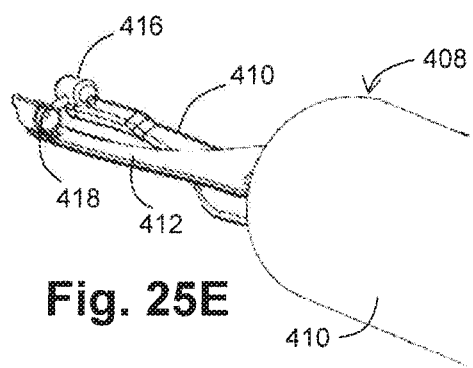

The fastening device includes first and second clamping arms 410, 412 that are pivotally mounted in a scissor arrangement for moving the distal ends of the arms toward and away from a closed, clamping condition, shown in FIG. 25E. The drive mechanism for clamp closure is a valve that rapidly forces the proximal sides of arms 410, 412 outwardly, acting to drive the distal end sides toward their clamping condition, although any suitable mechanical or pneumatic control mechanism may be employed.

The fasteners in device 408 are composed of male and female anchor components 416, 418, respectively, that are supplied to the distal clamping ends of the clamping arms through extendable/retractable supply channels 420, 422, respectively, shown in FIGS. 25B and 25C. A first pair of linear pushers (not shown) in the device function to advance anchor members within their associated supply channels. A second pair of retractable/extendable pushers (not shown) function to advance the two supply channels to an extended position, shown in FIG. 25C, for positioning a pair of anchor components at the distal ends of the clamping arms, and for retracting the two supply channels prior to a clamping and fastening operation, shown in FIG. 25E.

Figure 26A:
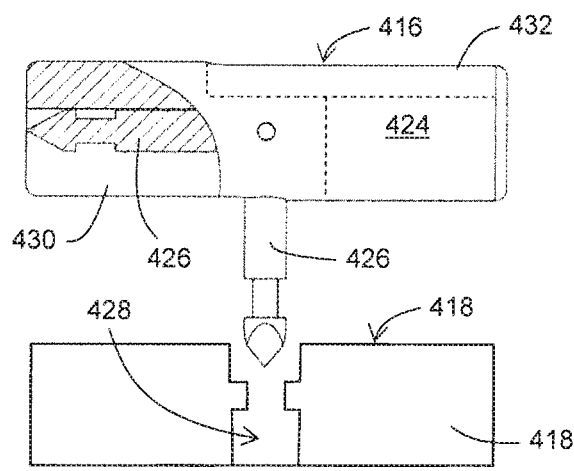
FIGS. 26A and 26B show components of a retractable-barb fastener used in the device 26A and the mechanism for portioning the barb (26B).
Figure 26B:
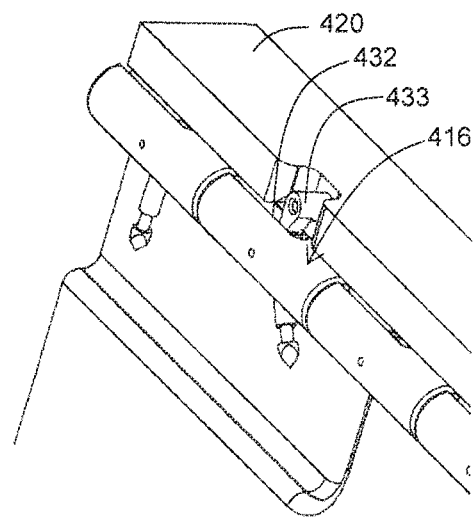

With reference to FIG. 26A, anchor component 416 has a barrel-shaped body 424 that has upper and lower grooves 430, 432, respectively, seen in FIGS. 26A and 26B. A barb 426 is mounted in the body, within groove 430, for pivoting movement between the retracted position seen in sectional outline in FIG. 26A and the extended, clamping position shown. Anchor component 418 has a barrel shaped body 419, and a cylindrical channel 428 formed in the body. As can be appreciated in FIG. 26A, the barb is designed to be locked within this channel when the two components are clamped together.

With reference of FIG. 26B, the distal end of supply channel 420 has a pivotally mounted detent 433 which rides within groove 432 of component 416 as the component is moved toward its distal end clamping position, engaging the associated barb in the component and moving it from its retracted to extended position.

In operation, the supply-tube pushers are first activated to advance the supply channels 420, 422 to a position where a single pair of anchor components is placed at the ends of the clamping arms, as indicated by the series of steps shown in FIGS. 25B-25D. With a pair of anchor members held at the distal ends of the arms, as shown in FIG. 25D, the supply tubes are retracted and the loaded clamp is positioned for clamping a tissue fold. The valve controlling clamping movement is now activated, squeezing the tissue fold and driving the male member barb through the tissue fold and into engagement with the female component, to fasten the fold. The clamp arms are then returned to their open condition, shown in FIG. 25A, readying the device for the next tissue fastening operation.

According to the invention, the barbed anchor fastener device is readily adapted for integration into each of the four tissue-acquisition devices described in Sections C-F above. For example, the fastener holder described with respect to each acquisition device may be modified to provide a feed tube by which the male anchor members in the present fastener can be advanced toward a distal-end clamping position, and the anvil described with respect to each acquisition device can be modified to provide a feed tube by which the female anchor members in the present fastener can be advanced toward an opposing distal-end clamping position.

Although the invention has been described with respect to specific aspects, embodiments, and applications, it will be appreciated that various changes and modification may be made without departing from the invention as claimed.

It is claimed:

1. A stapling device for fastening tissue, the device comprising:
    a tube that includes a lumen extending from a proximal end of the tube to a distal end of the tube; and
    a stapler head coupled to the distal end of the tube, the stapler head including an assembly coupled to an anvil at a first pivot, wherein the assembly includes:
    at least one staple;
    a first member coupled to a second member at a second pivot different from the first pivot; and
    an element disposed between the first member and the second member, the element being movable in a proximal-distal direction to pivot the second member relative to the first member, wherein the first member is first plate and the second member is a second plate, and wherein the element is in contact with planar surfaces of the first and second plates that face each other;
    wherein pivoting the assembly relative to the anvil moves the stapler head between an open configuration and a closed configuration; and
    wherein pivoting the second member relative to the first member in the closed configuration fastens the tissue with the at least one staple.

2. The device of claim 1, wherein the assembly includes a plurality of staples and a driver configured to engage, sequentially, each staple of the plurality of staples.

3. The device of claim 1, wherein the second member is disposed between the first member and the anvil.

4. The device of claim 1, wherein the stapler head further includes a flexible membrane coupled to the assembly and the anvil to define a chamber in communication with the tube.

5. The device of claim 1, wherein the assembly includes an arm extending from the first pivot to the second pivot.

6. The device of claim 1, wherein the proximal end of the tube is coupled to a shaft in communication with a source of vacuum.

7. A stapling device for fastening tissue, the device comprising:
    a housing coupled to an anvil, the housing containing:
        a cartridge configured to hold a plurality of staples in a linear array;
        a pusher assembly having a plurality of projections and a plurality of pusher elements configured to simultaneously engage an end of each staple of the plurality of staples; and
        an ejector assembly coupled to the pusher assembly, the ejector assembly including a first part and a second part each defining a plurality of slots, and each slot receiving a corresponding projection of the pusher assembly,
    wherein moving the first part relative to the second part of the ejector assembly causes the plurality of projections to move within the corresponding slots and causes the pusher elements to move towards the anvil.

8. The device of claim 7, wherein the anvil is parallel to the housing, the anvil being coupled to the housing by supports.

9. The device of claim 7, wherein the first part of the ejector assembly is movable relative to the second part along a longitudinal axis of the housing.

10. The device of claim 7, wherein the first part of the ejector assembly is slidable relative to the second part of the ejector assembly and slidable relative to the cartridge.

11. The device of claim 7, wherein each slot of the ejector assembly is defined by a surface of the first part that faces the cartridge or a surface of the second part of the ejector assembly that faces the cartridge.

12. The device of claim 7, wherein the first part is a first plate and the second part is a second plate, the first and second plates being coupled together and disposed on opposite sides of the cartridge.

13. The device of claim 7, wherein the plurality of slots extend in a direction transverse to a longitudinal axis of the cartridge.

14. The device of claim 7, wherein the cartridge includes a plurality of U-shaped slots, each of the slots configured to hold a staple.

15. A stapling device for fastening tissue, the device comprising:
    a housing coupled to an anvil, the housing containing:
        a cartridge defining a plurality of slots distributed in a linear array, each slot containing a staple;
        a pusher assembly having a plurality of pusher elements configured to simultaneously engage the plurality of staples to eject the staples from the cartridge as the pusher assembly moves towards the anvil, the pusher assembly further including a plurality of projections; and
        an ejector assembly including a first plate and a second plate movable relative to each other, wherein the cartridge is disposed between the first plate and the second plate;

wherein movement of the first and second plates relative to each other engages the pusher elements of the pusher assembly to eject the staples.

16. The device of claim 15, wherein the first and second plates are slidable relative to each other along a longitudinal axis of the housing, and the pusher elements are movable in a direction transverse to the longitudinal axis.

17. The device of claim 15, wherein the ejector assembly includes a plurality of slots defined by respective surfaces of the first and second plates facing the cartridge, and each slot of the ejector assembly houses a projection of the pusher assembly.

18. The device of claim 15, wherein the anvil is coupled to the housing proximate each of a first end and a second end of the anvil.

* * * * *